(12) United States Patent
Jenkins et al.

(10) Patent No.: US 7,349,523 B2
(45) Date of Patent: Mar. 25, 2008

(54) RADIATION ISOCENTER MEASUREMENT DEVICES AND METHODS AND 3-D RADIATION ISOCENTER VISUALIZATION SYSTEMS AND RELATED METHODS

(75) Inventors: Todd Perrin Jenkins, Greenville, NC (US); Ron Russell Allison, Greenville, NC (US); Claudio Sibata, Greenville, NC (US)

(73) Assignee: East Carolina University, Greenville, NC (US)

( * ) Notice: Subject to any disclaimer, the term of this patent is extended or adjusted under 35 U.S.C. 154(b) by 211 days.

(21) Appl. No.: 11/171,729

(22) Filed: Jun. 30, 2005

(65) Prior Publication Data
US 2006/0002519 A1 Jan. 5, 2006

Related U.S. Application Data

(60) Provisional application No. 60/584,670, filed on Jul. 1, 2004.

(51) Int. Cl.
*A61N 5/10* (2006.01)
(52) U.S. Cl. .................. 378/65; 378/163; 378/205
(58) Field of Classification Search ............... 378/65, 378/163, 205
See application file for complete search history.

(56) References Cited

U.S. PATENT DOCUMENTS

| | | | |
|---|---|---|---|
| 5,430,308 A * | 7/1995 | Feichtner et al. | 250/580 |
| 5,458,125 A * | 10/1995 | Schweikard | 600/407 |
| 6,011,828 A | 1/2000 | Hardy et al. | |
| 6,535,574 B1 | 3/2003 | Collins et al. | |
| 6,668,073 B1 * | 12/2003 | Robar et al. | 382/128 |
| 6,851,855 B2 * | 2/2005 | Mitschke et al. | 378/207 |
| 6,865,253 B2 * | 3/2005 | Blumhofer et al. | 378/65 |
| 6,904,125 B2 * | 6/2005 | Van Dyk et al. | 378/65 |
| 2002/0193685 A1 | 12/2002 | Mate et al. | |
| 2004/0120560 A1 | 6/2004 | Robar et al. | |
| 2006/0203967 A1 * | 9/2006 | Nilsson | 378/207 |

FOREIGN PATENT DOCUMENTS

GB    2390964    1/2004

OTHER PUBLICATIONS

International Search Report and Invitation to Pay Additional Fees, dated incorrectly as mailed Dec. 16, 2005 for corresponding PCT application No. PCT/US05/023668.
International Search Report and The Written Opinion of the International Searching Authority, mailed Mar. 22, 2006 for corresponding PCT application No. PCT/US05/023668.

* cited by examiner

*Primary Examiner*—Edward J. Glick
*Assistant Examiner*—Thomas R. Artman
(74) *Attorney, Agent, or Firm*—Myers Bigel Sibley & Sajovec PA

(57) ABSTRACT

A three-dimensional phantom assembly for use with a radiation treatment device includes a three-dimensional support member having at least two, spaced apart opposed surfaces configured to hold at least one generally planar radiation sensitive dosimeter sheet such that the dosimeter sheet generally conforms to a shape defined by the two opposed surfaces. During irradiation, a radiation beam trajectory passes through the two opposed surfaces. Related systems methods for determining a radiation isocenter and/or generating a 3-D visualization of the radiation isocenter using radiation patterns obtained using a phantom are also described.

10 Claims, 23 Drawing Sheets
(3 of 23 Drawing Sheet(s) Filed in Color)

130A

US 7,349,523 B2

RADIATION ISOCENTER MEASUREMENT DEVICES AND METHODS AND 3-D RADIATION ISOCENTER VISUALIZATION SYSTEMS AND RELATED METHODS

RELATED APPLICATIONS

This application claims the benefit of priority to U.S. Provisional Patent Application Ser. No. 60/584,670 filed Jul. 1, 2004, the contents of which are hereby incorporated by reference as if recited in full herein.

FIELD OF THE INVENTION

The present invention relates to methods and devices for measuring distances to a subject for therapies employing radiation.

BACKGROUND OF THE INVENTION

Patients undergoing radiation therapy are typically placed on a treatment platform of a radiation treatment gantry. The gantry has a radiation source that is used to generate a radiation beam that irradiates a region of interest in the patient, such as diseased tissue including a tumor or cancerous growth site. Although the radiation can reduce the amount of diseased tissue, it can also have a harmful effect on the healthy tissue surrounding the diseased tissue. Thus, it is generally desirable to deliver the lowest effective dose of radiation localized with respect to the targeted tissue.

When delivering the radiation, a plurality of beams of radiation may be directed to the target area of interest from several positions outside the body. The gantry can be rotated to provide the radiation beams from different positions. The point at which the beam trajectories converge or intersect is generally referred to as the isocenter. The isocenter typically receives the largest radiation dose because of the cumulative radiation received from multiple radiation beams.

Conventionally, an image guided radiation therapy (IGRT) system generally uses an image of a patient to choose a location for the treatment plan isocenter. The patient is positioned in the treatment device based on image information and the isocenter of the machine. The dose received by the patient at the isocenter can be estimated by measuring the radiation dose in a phantom device. Some phantom devices may be configured to simulate radiation exposure of the body, for example, by using a solid or liquid material that mimicks the composition of the body, and may include dosimeters for determining a radiation dose at and around the isocenter.

SUMMARY OF THE INVENTION

Embodiments of the present invention provide a three-dimensional phantom assembly for use with a radiation treatment device with at least two opposed, spaced apart surfaces configured, during irradiation, to allow a radiation beam trajectory to pass through the two opposed surfaces.

The three-dimensional support member can be configured to hold at least one generally planar radiation sensitive media that generally defines and/or conforms to a shape defined by the two opposed surfaces, wherein during irradiation, a radiation beam trajectory passes through the two opposed surfaces.

In some embodiments, the device can releasably hold the at least one dosimeter sheet. In some embodiments, the device includes reference indicia configured to project a reference coordinate with respect to the support member to a dosimeter sheet held by the support member. For example, the reference indicia may be held by (disposed on and/or in) the support member.

In some embodiments, the support member includes a plurality of spaced apart generally planar members that define the at least two, spaced apart surfaces. The device can include a dosimeter sheet that can include one or more sheets of film and/or charge coupled device (CCD) screens.

In particular embodiments, the opposed surfaces include three opposed surfaces that form a generally triangular cross section. The generally triangular cross section may be an equilateral triangle. The support member can include a first planar member connected to and parallel to a second planar member such that a dosimeter sheet is releasably positioned (sandwiched) between the first and second planar members. The first and second planar members can include plexiglass.

In some embodiments, an isocenter location marker is positioned at a fixed location with respect to the support member, typically at the centroid of the support member. The isocenter location marker may include a radiopaque reference and/or fiducial marker that can be identified in a digitized image of an x-ray of the phantom.

Some embodiments are directed to methods of determining an isocenter location of a radiation treatment device. The methods include: (a) irradiating at least one radiation sensitive media on a three-dimensional phantom having a geometric shape with at least two opposed sides using a first radiation beam location having a first trajectory that passes through the two opposed surfaces at a first entrance position and a first exit position; (b) irradiating the at least one dosimeter sheet using a second radiation beam location having a second trajectory that passes through the two opposed surfaces at a second entrance position and a second exit position; and (c) programmatically determining an intersection between the first trajectory and the second trajectory to estimate an isocenter.

In some embodiments, the intersection between the first trajectory and the second trajectory is based on the first and second entrance positions, the first and second exit positions, and the reference coordinate. The dosimeter sheet can be irradiated so that the reference indicia can be electronically used to identify the reference coordinate on the dosimeter sheet.

In some embodiments, estimated isocenter of the radiation treatment device can be estimated prior to irradiation. An isocenter reference location is positioned at the estimated isocenter. The intersection point between the first trajectory and the second trajectory is compared to the isocenter reference location to evaluated the estimated isocenter.

According to further embodiments of the present invention, methods of evaluating an isocenter location of a radiation treatment device include: (a) obtaining a plurality of two dimensional digital images of radiation patterns taken from a plurality of different sides of a three-dimensional phantom; and (b) electronically generating a three-dimensional visual representation of a radiation isocenter using data from the two dimensional digital images.

The radiation patterns can correspond to an entrance radiation pattern providing a corresponding image having a plurality of lines that intersect in one location.

Some methods of determining an isocenter location of a radiation treatment device include defining a reference coordinate system with respect to a three-dimensional phantom device using a reference location based on data obtained from a generally planar dosimeter sheet irradiated while supported by the phantom device. A spaced apart entrance location and an exit location is determined for at least two different beam trajectories based on data obtained from the irradiated dosimeter sheet. An intersection between the at least two beam trajectories is determined with respect to the reference coordinate system of the phantom device based on the at least two beam trajectories to define an isocenter. Computer program products may also be provided.

In some embodiments, an isocenter is defined with respect to the reference coordinate system in the phantom device. The defined isocenter can be compared to the estimated system isocenter to provide a deviation between the true and estimated system isocenters. The deviation may be defined in terms of X, Y and Z dimensions or other coordinate system dimensions.

Some embodiments are directed to computer program products for determining or evaluating an isocenter location of a radiation treatment device. The computer program product includes a computer readable medium having computer readable program code embodied therein. The computer readable program code includes: computer readable program code that is configured to convert a plurality of two dimensional digital images of radiation patterns taken from a plurality of different sides of a three-dimensional phantom into a three-dimensional visual representation of location and size of a radiation isocenter using data from the two dimensional digital images and data associated with a known geometric shape of the phantom.

Still other embodiments are directed to systems of generating 3-D visualizations of a radiation isocenter of a radiation treatment system. The systems include: (a) a radiation treatment system; (b) a three-dimensional phantom having a known geometric shape and center; and (c) a processor having computer readable medium having computer readable program code embodied therein. The computer readable program code includes computer readable program code that is configured to convert a plurality of two dimensional digital images of radiation patterns taken from a plurality of different sides of the three-dimensional phantom into a three-dimensional visual representation of a radiation isocenter using data from the two dimensional digital images.

In some embodiments, the system can also include computer program code that calculates any deviation from a calculated center of a phantom to the radiation isocenter of the radiation treatment system using data from the digital images of the radiation patterns. The radiation patterns of the digital images comprise an entrance radiation pattern and at least two corresponding exit radiation patterns, with the entrance radiation pattern comprising a plurality of lines that have at least one intersecting position in the image.

Still other embodiments are directed to a quality assurance evaluation kit adapted for use with a phantom having a three-dimensional geometric shape with a known center for quality assurance evaluations of radiation treatment isocenters. The kits include at least one radiation sensitive dosimeter sheet configured to conform to at least one side of a phantom having a generally triangular cross-sectional shape, the at least one radiation sensitive dosimeter sheet having at least one reference indicia of a phantom side and/or front to back location relative to a position on the phantom.

These and other objects and/or aspects of the present invention are explained in detail in the specification set forth below.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF EMBODIMENTS OF THE INVENTION

Figure 1A:
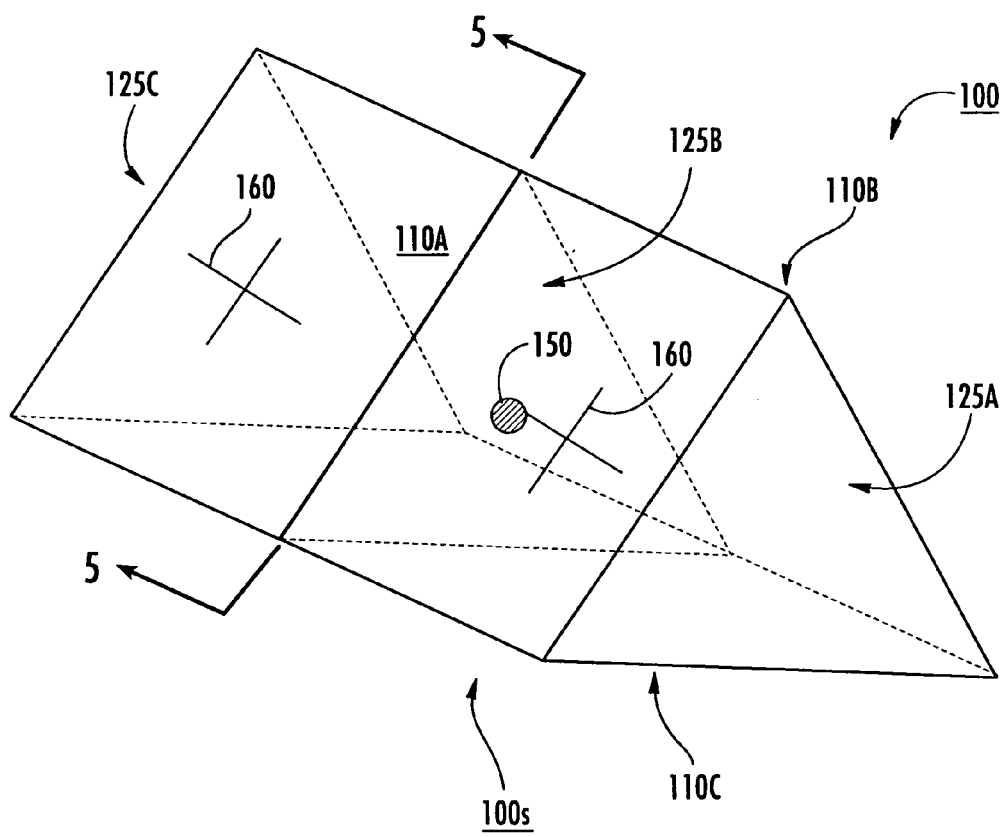
FIG. 1A is a perspective view of a phantom device according to embodiments of the present invention.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations, unless specified otherwise. In addition, the sequence of operations (or steps) is not limited to the order presented in the claims unless specifically indicated otherwise. Where used, the terms "attached", "connected", "contacting", "coupling" and the like, can mean either directly or indirectly, unless stated otherwise.

As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The term "automated" and "automatic" refers to operations that are carried out without requiring manual assistance and are typically carried out electronically and/or programmatically. The term "electronic" means that the system, operation or device can communicate using any suitable electronic media and typically employs programmatically controlling the communication between participants using a computer network. The term "programmatically" means employing computer programs to control or direct operations such as calculations, 2-D to 3-D conversions of spatial representations and the like. The programmatic direction can accept manual or user input and/or may automatically operate to provide desired electronic and/or visual data.

When an element is described as being formed "on" or "adjacent to" another element, the element may be formed directly on the other element, or other elements may be interposed therebetween. In contrast, when an element is referred to as being "directly on" another element, there are no intervening elements present. The thicknesses of elements, layers or regions may be exaggerated for clarity.

As used herein, a "phantom" is a device that can be placed in a radiation treatment device to obtain data of radiation parameters associated with a radiation treatment plan, and/or a radiation system set-up or operational evaluation, that is typically used for quality assurance or calibration purposes, such as to confirm that a planned treatment directs radiation to a target region, to evaluate the radiation isocenter of the device and/or that equipment setup is proper.

The terms "reference indicia" and "fiducial marker" refer to at least one electronically detectable landmark or locational feature associated with the phantom and/or radiation sensitive media that can be used to register one or more X-ray images to different sides of the phantom and/or location on the phantom. Typically, the phantom is configured with multiple fixed location reference indicia or fiducial markers that are embedded in the phantom to inhibit movement. The phantom can have at least one reference indicia and/or fiducial marker for each side of the phantom that is configured to hold a discrete radiation (X-ray) sensitive media (such as dosimeter sheets or film or charge coupled devices "CCD"s). The X-ray image can be digitized and the reference indicia or fiducial markers can be optically programmatically automatically recognized in the digitized image (with or without image enhancement) and used to electronically register the orientation and/or position of the digitized image.

Figure 1B:
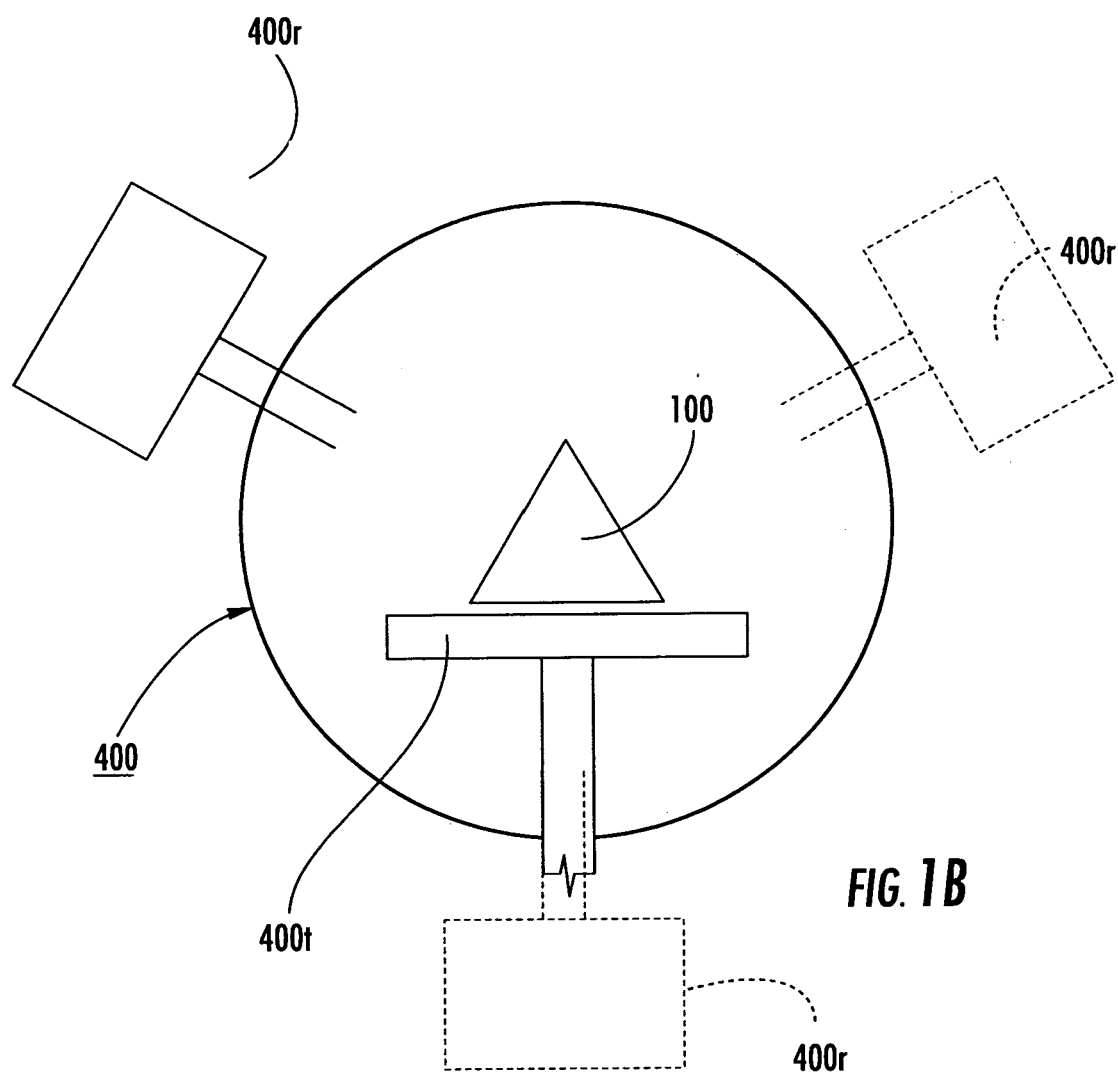
FIG. 1B is a schematic illustration of a radiation treatment system with the phantom of FIG. 1A held on a patient treatment table according to embodiments of the present invention.

As shown in FIG. 1A, some embodiments of the invention are directed to a three-dimensional phantom assembly 100 for use with a medical radiation treatment device. The phantom device 100 can be placed in a radiation treatment device for verification of equipment radiation isocenter, particularly systems that are configured to deliver a relatively complex radiation treatment, typically by generating multiple beams and shaping (collimating, filtering or otherwise shaping) and delivering from multiple directions to a target treatment region in the body. As shown in FIG. 1B, the radiation source 400r associated with the radiation treatment system or device 400 can be translated relative to a patient table 400t to project the beam into the target region having a radiation treatment isocenter, from different planes. An exemplary radiation treatment device that can be used with the phantom device 100 is a linear accelerator ("LINAC"). A LINAC can use microwave energy to accelerate electrons, which impinge on a heavy metal target to produce high-energy X-rays. Other radiation sources can be used, as is well known to those of skill in the art, including, but not limited to cobalt 60. One exemplary system is a Siemens™ Primus™ or MD2™ radiation treatment device available from Siemens Corporation, New York City, N.Y., U.S.A. The phantom assembly 100 can be used to verify set-up for each patient or may be used at desired intervals, such as daily, weekly or monthly, or at other desired times to verify that the equipment radiation isocenter substantially matches with the isocenter defined by data obtained using the phantom 100. If not, system can be re-calibrated to a desired operating standard.

The phantom assembly 100 can have a geometry that has at least two spaced-apart, opposed surfaces, shown as having three primary opposing surfaces 110A, 110B and 110C. Generally stated, during irradiation, a radiation beam has a trajectory that generates a pattern on at least two of the opposed surfaces. In operation, data obtained using the phantom 100 can be used to identify beam trajectories registered to the side of the respective side of the phantom 100. As shown, the phantom assembly 100 can have an elongate generally triangular cross-sectional or end view profile shape. However, other geometries having a known center and surfaces that can generate appropriate beam trajectories may also be used, such as a pentagon, hexagon, cube, sphere and the like, where sufficient radiation beam patterns can be obtained to define beam projections in space.

In operation, as a beam is generated and transmitted to the phantom 100, it has an entering location and pattern and an exit location and pattern(s). The entrance beam can have a relatively complex shape, such as a plurality of lines with at least one intersecting point (see FIGS. 7, 15, with lines 182A) as will be discussed further below. The beam trajectory detected by media on the opposed surfaces of the phantom assembly 100 can be evaluated to determine the isocenter of the radiation system. The position that the beam enters the phantom assembly 100 and the position that the beam exits the phantom can be detected. A plurality of beams can be used to expose media held by the phantom 100 during a quality assurance or calibration event, each having associated beam trajectories. The intersection(s) between the trajectories can be determined to measure the isocenter of the radiation treatment device relative to the isocenter of the phantom 100. As shown, at least two (FIG. 7), and typically at least three (FIG. 15), lines that cross over at at least one location can be used to provide the entrance beam pattern.

Figure 5:
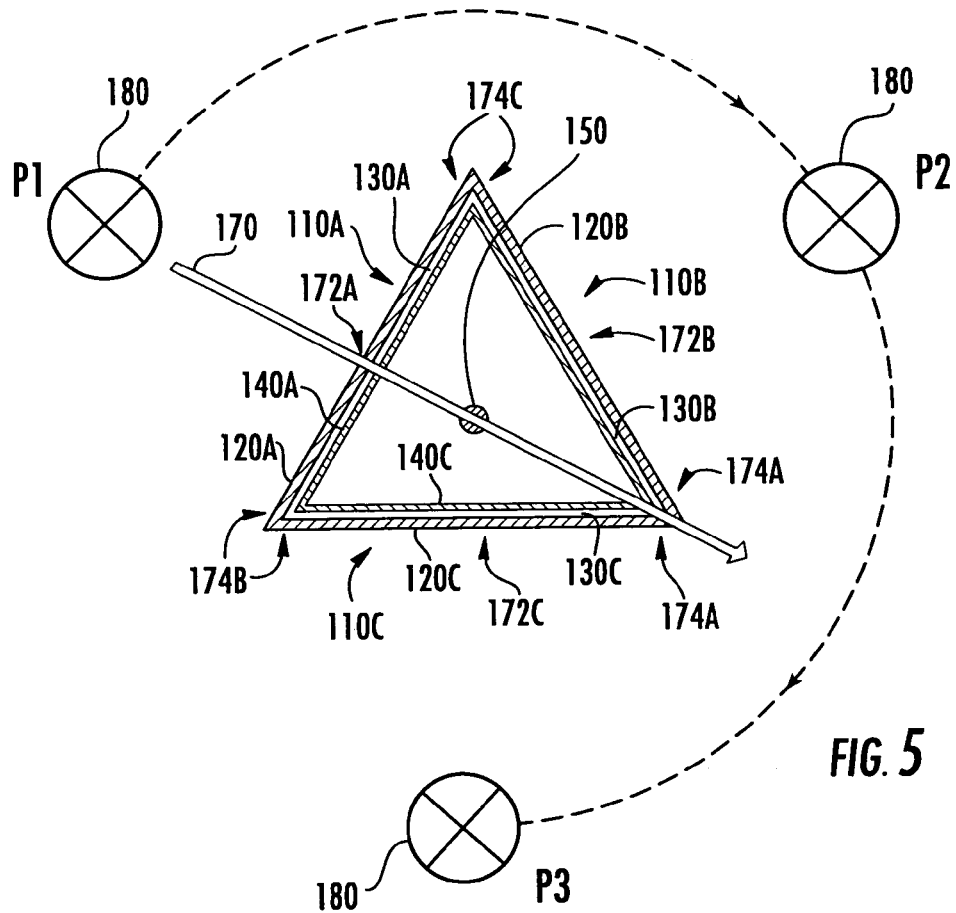
FIG. 5 is a cross-sectional view taken across line 5-5 of the phantom device of FIG. 1A.

Various types of radiation sensitive media can be used that can be mounted to the phantom 100. For ease of discussion, the figures will be discussed primarily with respect to a generally planar dosimeter (X-ray) detection media such as at least one generally planar radiation sensitive dosimeter sheet (film) that generally conforms to the shape of the phantom 100. In some embodiments, two or more discrete dosimeter sheets may be respectively positioned on opposite surfaces of the phantom assembly 100. FIG. 5 illustrates three sheets, 130A, 130B, 130C, each substantially conformally covering substantially all of the respective side of the phantom that it is mounted to. However, it should be understood that a single dosimeter sheet may be used such that the sheet may be folded or bent to substantially conform to a plurality of sides of the phantom body 100. Examples of dosimeter sheets or film include radiation sensitive film (X-Omat V™, commercially available from Eastman Kodak Company, Rochester, N.Y. (U.S.A.)). Another type of dosimeter detection media comprises a charge coupled device (CCD) screens, such as amorphous silicon flat panel X-ray detectors. Combinations of these devices may be used. Where used, the dosimeter sheets can be releasably held by the phantom 100 so that the dosimeter sheets may be removed for further processing (exposed and digitized) and/or replaced with unexposed sheets. However, dosimeter media that may be reusable for multiple isocenter measurements may also be used. For example, as noted above, CCD screens may be permanently fixed to the device and multiple isocenter measurements may be taken. The image dosimeter media can be used to determine the location and/or radiation dose of the isocenter evaluation radiation beam. For ease of discussion, the term "dosimeter sheets" will be used hereafter to designate either film or CCD's.

As illustrated in FIGS. 1-5, the three-dimensional phantom device 100 includes a support member 100s with three primary opposing surfaces 110A, 110B and 110C, that are configured to releasably hold generally planar radiation sensitive dosimeter sheets 130A, 130B and 130C, respectively (FIG. 5).

Phantom devices according to embodiments of the present invention may be formed of materials that generally allow a radiation beam to pass through the device, such as elastomeric materials including plexiglass, acrylic, polystyrene, plastics and/or other materials such as aluminum and wood. The surfaces of the support member can define an interior cavity that may be generally hollow or air-filled; however, the interior cavity may alternatively be filled with a material that allows the radiation beam to pass through the device, for example, a material that generally does not interact with the radiation beam or interacts with the radiation beam to a nominal degree that allows sufficient beam penetration to provide entrance and exit marks on the dosimeter sheets. For example, phantom devices according to embodiments of the present invention may be filled with polystyrene. The device does not necessarily use a material that mimics the irradiation interactions of a body (such as water-equivalent plastics) as is often used in conventional phantom devices, although such materials may be used. The device can be structurally sufficiently rigid to maintain a desired geometric shape when holding the radiation sensitive receiving medium, yet relatively light-weight for portability and/or ease of use. The phantom device can have primary surfaces or walls that are generally planar and sufficiently rigid to hold dosimeter film or sheets or CCD's. Although the primary surfaces of the phantom body may be continuous, a non-continuous support member (such as a frame configuration) may also be used to define a surface and hold the dosimeter sheets or CCD's and the like, in position.

In some embodiments, a reference coordinate can be projected to the dosimeter sheet(s) held by the support member of the phantom assembly 100 using reference indicia placed on, in or adjacent each selected phantom wall(s). For example, the reference indicia can be configured to generate a corresponding image onto the dosimeter sheet(s) or CCD. Thus, the reference indicia in the image can be digitized with the X-ray image and the optical data used to define a location and/or coordinate system with respect to the phantom 100. The intersection between two or more radiation beams can be used to estimate an isocenter in the coordinate system of the phantom assembly.

Figure 3:
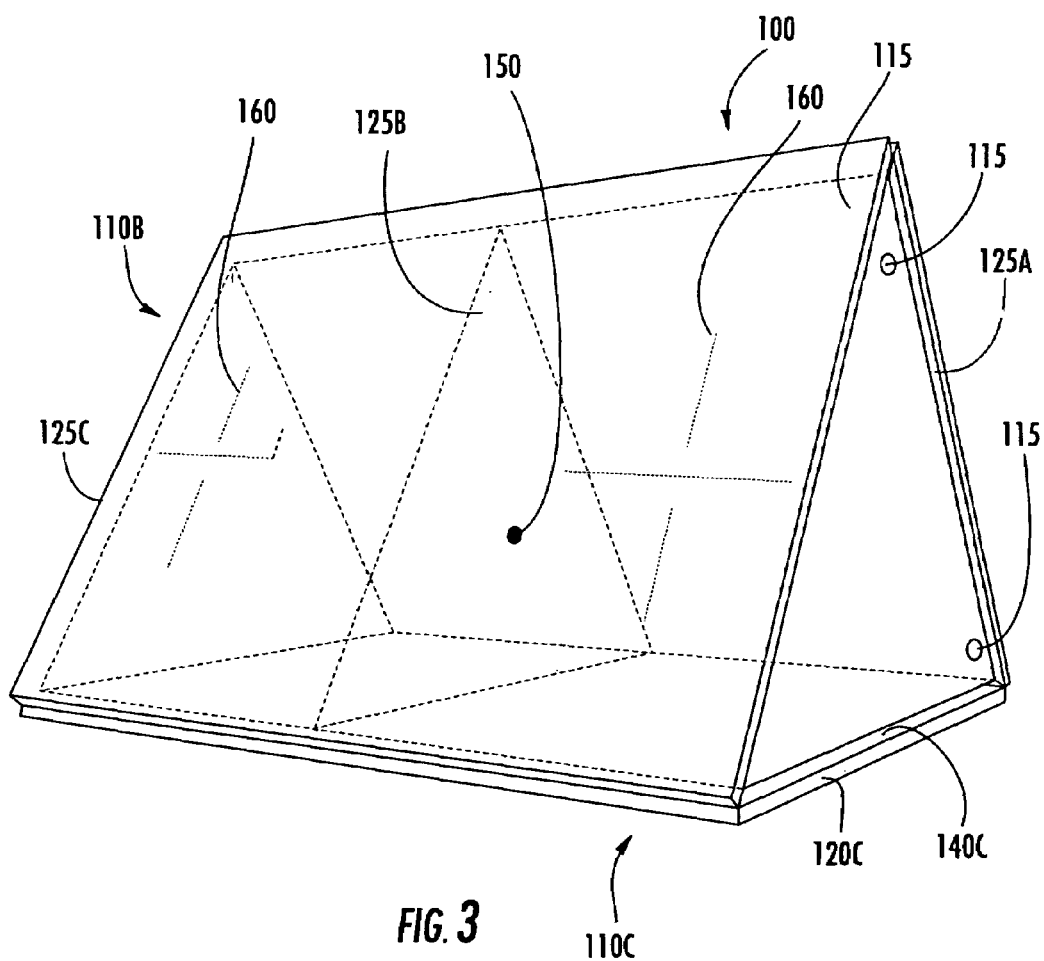

As shown in FIG. 3, phantom devices 100 according to embodiments of the present invention include an isocenter location marker 150 positioned at a known interior position (having a known X, Y and Z position or other coordinate system position).

Typically, the isocenter location marker 150 is positioned at the center of the phantom 100. As shown, an interior triangle is disposed in the middle of the phantom substantially orthogonal to three opposed surfaces and/or perimeter sides, 110A, 111B, 110C. The isocenter location marker 150 resides in the center of the interior member 125B, between the opposed surfaces of the phantom in the center of the phantom body 100. The isocenter marker can be suspended from a support line, or otherwise disposed in the phantom 100. The center of the phantom 100 may also be virtually generated in a digitized image based on the known geometry of the phantom 100 and data from the reference indicia or fiducial marks formed in the X-ray images based on locational indicia or marks in the film and/or on the phantom.

During a calibration or quality assurance event, the phantom 100 can be placed on a patient table in an aligned position in the radiation treatment system so that he phantom has a desired orientation and position relative to an estimate system isocenter location (which may be defined by projecting lasers and the like). In some embodiments, the isocenter location marker 150 may be positioned in the estimated isocenter of the radiation treatment device, using, for example, imaging and/or positioning techniques known to those of skill in the art. The isocenter location marker 150 may comprise radiopaque indicia, such as a lead mark, wire or spot that may occupy less than about 2 mm in a scale size of the digitized image, and typically occupies a submillimeter space that is less than about 1 pixel. However, the location marker 150 can be any size and shape that is visually (optically) useful to indicate an isocenter location. The intersection between two or more radiation beams can be used to verify the positioning technique used and/or to evaluate the estimated isocenter of the radiation treatment device.

In some embodiments, phantom devices 100 are described herein with respect to a substantially symmetric configuration in which three dosimeter sheets form an equilateral triangular cross section. However, as noted above, other configurations may be used. For example, a dosimeter sheet can be held on a phantom that generally forms a sphere or cube such that the sheet covers a major surface area of the support member. Two dosimeter sheets may be held on a support member such that the sheets are spaced apart from and parallel to one another, e.g., a first and second sheet placed on opposed surfaces of a cube. The dosimeter sheets can be irradiated from opposite directions so that one radiation beam passes in a direction from the first sheet to the second sheet and another radiation beam passes in a direction from the second sheet to the first sheet. The radiation beam trajectories may be off-axis with one another or the trajectories may share a common axis through the center of the dosimeter sheets.

As illustrated in FIGS. 2-5, each surface 110A, 110B, and 110C can include an inner planar member 140A, 140B, 140C, respectively, and a corresponding outer planar member 120A, 120B, 120C, respectively. The respective pairs of planar members 120A and 140A, 120B and 140B, and 120C and 140C can be releasably attached together to form a generally continuous perimeter shape. The elongate generally triangular body of the phantom 100 may have closed ends 125A, 125B (FIG. 3) or open ends (FIG. 2) or one closed and one open end (not shown).

In some embodiments, the phantom 100 may include a single wall on one or more primary surface. In any event, the walls of the phantom can include attachment means to hold the dosimeter media in position, such as, for example, pegs 115 in the outer planar members 120A, 120B and 120C that may be inserted into apertures in the inner planar members 140A, 140B and 140C. In other embodiments, pegs 115 or other matable attachment means can be positioned in the inner wall and received in apertures on the outer wall. Other attachment means such as fastening devices or materials can be used, including adhesives, clips, screws, VELCRO, tape (Such as double sided tape), and the like to hold the outer planar members 120A, 120B and 120C and the inner planar members 140A, 140B and 104C in position and/or to hold the dosimeter sheets 130A, 130B and 130C on the phantom device 100.

Figure 4:
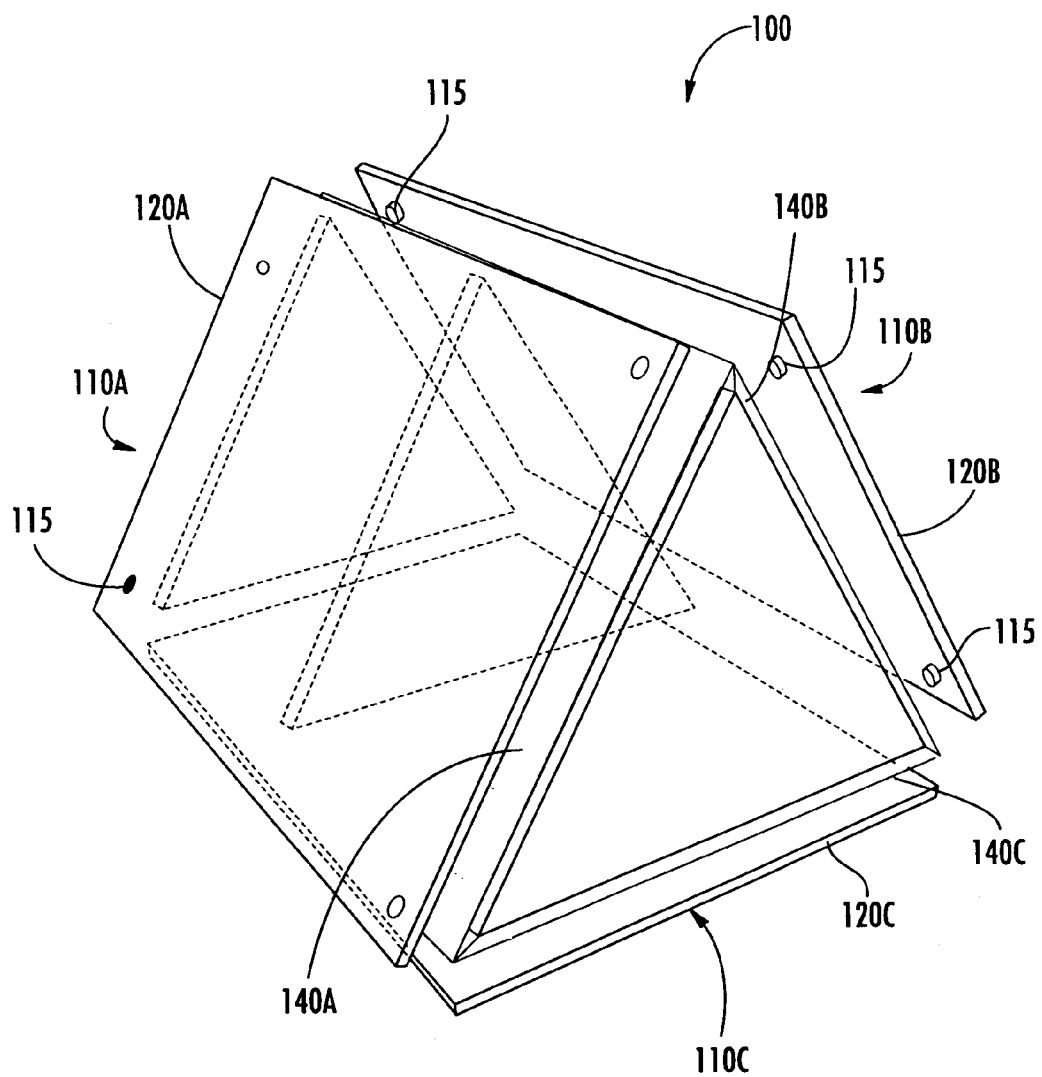
FIG. 4 is an exploded perspective view of the phantom device of FIG. 1A.

FIGS. 3 and 4 illustrate that the three-dimensional phantom device 100 can include surfaces 110A, 110B and 110C positioned adjacent optional two end planar members 125A and 125C and an optional inner planar member 125B. As discussed above, the radiopaque marker 150 is held by the inner (planar) member 125B at a position in a central region of the device 100. The planar members 120A, 120B, 120C, 125A, 125B, 125C, 140A, 140B and 140C are formed of a material (such as the materials described above) that generally does not unduly inhibit the transmission of a radiation beam and/or generally does not interact with the radiation beam or interacts at a level that is sufficiently low so as to not result in significant readings on the dosimeter sheets 130A, 130B and 130C.

Figure 2:
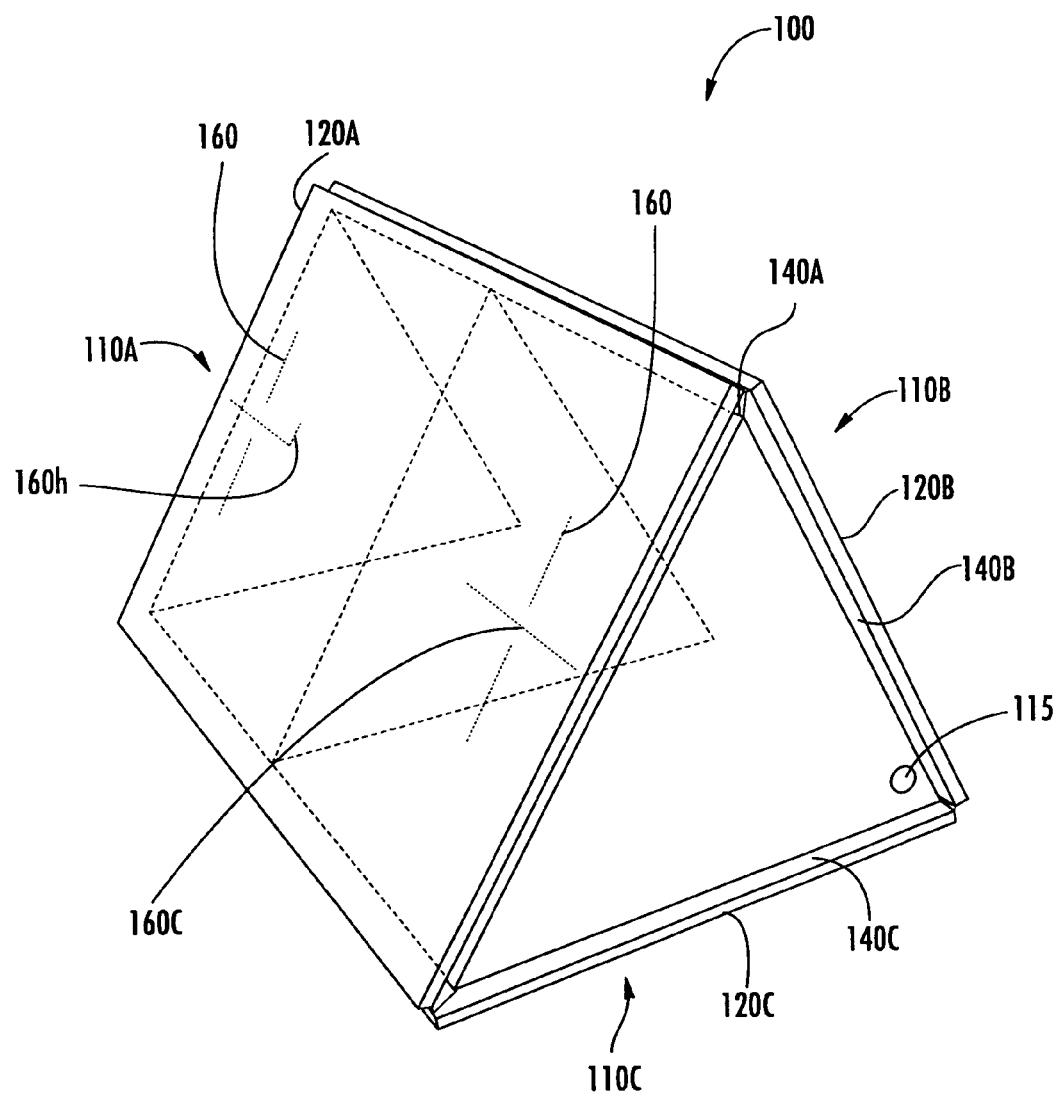
FIGS. 2-3 are perspective views of the phantom device of FIG. 1A from opposing sides of the phantom device.

As illustrated in FIG. 5, the dosimeter sheets 130A, 130B and 130C can be held between the inner planar members 140A, 140B, and 140C and the outer planar members 120A, 120B, and 120C. As shown in FIGS. 1-4, reference indicia 160 are positioned on the outer planar members 120A, 120B, and 120C. As shown in FIG. 2, the reference indicia 160 may be elongate marks, such as elongate linear marks with cross-shaped hairline marks (shown with open centers 160c and an optically distinctive hook or leg on one edge 160h) that are positioned to provide a reference position to the dosimeter sheets 130A, 130B and 130C held by the phantom device 100. For example, the indicia 160 can be provided by any material or coating that can generate an optically (electronically) detectable image on the dosimeter sheets 130A, 130B and 130C. In some embodiments, the indicia 160 may be formed of wire that generates a corresponding image on the dosimeter sheets 130A, 130B and 130C. In some embodiments, the device 100 is irradiated with a large aperture beam to expose the portions of the dosimeter sheets 130A, 130B and 130C that are adjacent the indicia 160. The device 100 may be exposed to such a beam before or after the dosimeter sheets (or CCD's) 130A, 130B and 130C are irradiated with beam trajectories that are used to determine the isocenter. The indicia 160 may comprise steel wires, although other suitable materials, such as lead or tungsten may be used to produce distinct marks in images of the dosimeter sheets 130A, 130B and 130C, for example, after exposure to radiation. The marks can be used to provide a reference position of the dosimeter sheets 130A, 130B and 130C to the phantom 100. For example, the images of indicia 160 can be used to define a coordinate system with respect to the position of the dosimeter sheets 130A, 130B and 130C (and any developed feature thereon) and the phantom device 100.

The phantom device 100 can be used to test and/or calibrate patient and isocenter positioning and/or locating techniques associated with radiation treatment devices. For example, the device 100 can be positioned in a radiation treatment device and irradiated such that the indicia 160 generate patterns on the dosimeter sheets 130A, 130B and 130C. The patterns may be visible after the sheets 130A, 130B and 130C are exposed (and where film is used, after the sheets 130A, 130B and 130C are developed) to create a digitized image. The indicia 160 in the image can be used to define a reference location and/or coordinate system so that the location of other features developed on the dosimeter sheets 130A, 130B and 130C may be determined with respect to the device 100. In some embodiments, the dosimeter sheets 130A, 130B and 130C may be irradiated from a plurality of external beam source positions such that radiation beams from the different positions provide image features (such as lines or other marks) to the dosimeter sheets or CCD's 130A, 130B and 130B that can be used to determine the trajectory of the respective radiation beams. The trajectories can be used to determine an isocenter of the radiation treatment device in a coordinate system defined by the reference marks formed in the image.

As shown, for example, in FIG. 5, the device 100 can be irradiated from a plurality of positions, such as P1, P2 and P3. For example, if a radiation treatment device is positioned at P1, a radiation beam having a cross sectional shape 180 (with a plurality of lines that intersect as shown by the pattern proximate P1) may be projected across a trajectory direction 170. The radiation beam can be shaped or collimated to provide the cross sectional shape 180, for example, by using one or more exposures along this trajectory. For example, an intersecting line or "cross" shape can be formed with a plurality of images of a line that is rotated or translated at certain angles, such as between about thirty to about ninety degrees.

As illustrated by the schematic views proximate P1, P2 and P3, the evaluation beam can be an "X" shaped beam whereby two or more lines crossover each other at an intersection point. In some embodiments, the cross sectional shape 180 of the beam is a "cross" shape. The center of the "cross" or consequently, the center of the radiation beam line, can be ascertained by the intersection of the two lines that form the "crossover" or intersecting shape of the shape 180. Other shapes of entrance beams may be used. In some embodiments, the shape of the radiation beam may be rotated or altered to distinguish between beams on the dosimeter sheets. For example, if radiation beam trajectories share a common axis, the radiation beam shape may be modified so that the resulting entrance and exit marks formed by one radiation beam on the dosimeter sheets may be distinguished from entrance and exit marks formed by another radiation beam from a different direction. The radiation beams may be rotated or shaped differently to provide distinctive marks on the dosimeter sheets that correspond to a specific radiation beam direction.

Still referring to FIG. 5, in operation, a first radiation beam enters the phantom 100 at an entrance zone 172A and exits the phantom at an exit zone 174A. The radiation beam irradiates an area on the dosimeter sheet 130A in the shape of the cross sectional shape 180 of the beam in the vicinity of the entrance zone 172A. The radiation beam also irradiates an area on the dosimeter sheets 130B and 130C in the vicinity of the exit zone 174A. Second and/or third radiation beams can also irradiate the dosimeter sheets 130A, 130B and 130C from positions P2 and/or P2.

The entrance zone 172A and the exit zone 174A are spaced apart such that a trajectory direction 170 can be determined based on the position of the entrance zone 172A and the corresponding exit zone 174A. Radiation beam trajectory directions can similarly be observed and/or calculated from radiation beams at positions P2 and/or P3. A radiation beam from position P2 may enter the phantom 100 at an entrance zone 172B and exit at an exit zone 174B. Similarly, a radiation beam from position P3 may enter the phantom at an entrance zone 172C and exit at an exit zone 174C. An intersection between two or more trajectories can be determined based on the respective entrance positions and exit positions. The position of the intersection of the beam trajectories with respect to the device 100 can be determined based on a reference location defined by the imprint from the indicia 160 on the dosimeter sheet. Data corresponding to the intersection between the beam trajectories can be used to determine the isocenter of the radiation beams from the radiation treatment device.

In some embodiments, the measured entry and exit positions of the radiation trajectories may be corrected during analysis if the location of the radiation "cross over" differs by some known amount from the true center of the radiation beam line. The device 100 can be designed such that this offset can be measured along with the primary isocenter measurement.

Figure 6:
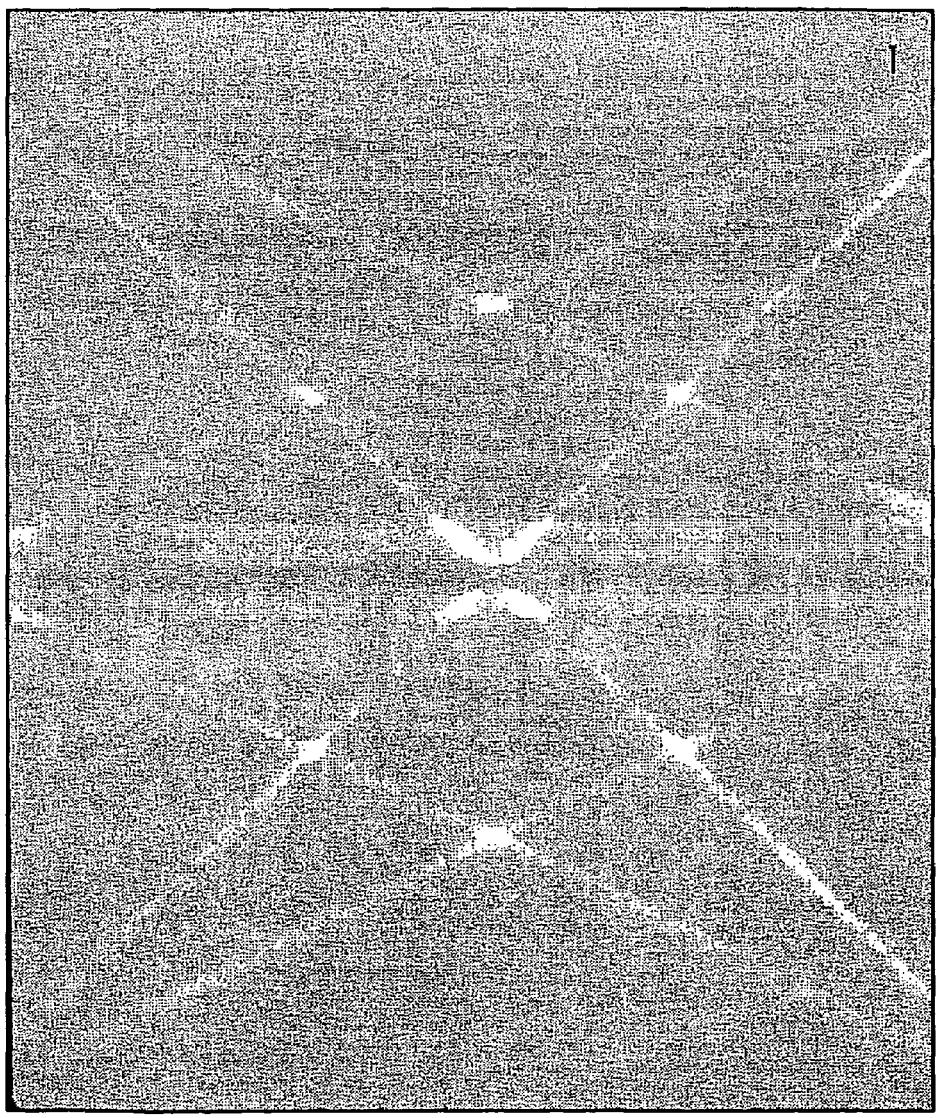
FIGS. 6-7 are views of an exposed, developed and analyzed radiation sensitive film after the film has been removed from the phantom device of FIG. 1A.
Figure 7:
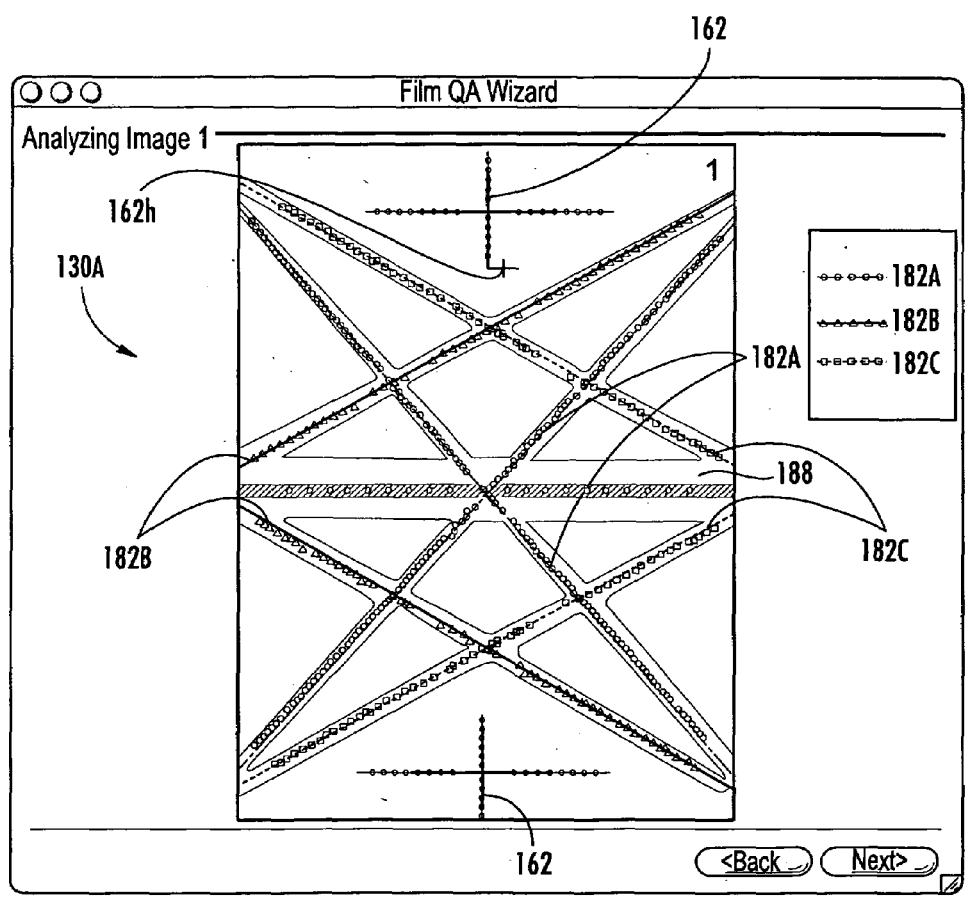

An example of the dosimeter sheet 130A after exposure from beams generated from P1, P2 and P3, reference indicia exposure, and subsequent image development is shown in FIGS. 6-7. The image on the dosimeter sheet 130A in FIG. 6 is typically digitized, such as scanned into electronic form and enhanced as shown in FIG. 7 using enhancing techniques such as contrast enhancement and histogram equalization. For example, ImageJ™ is a software product available through the National Institutes of Health, U.S.A., that can enhance images in this manner. Other image enhancement software may be used as is known to those of skill in the art. As illustrated in FIG. 7, the dosimeter sheet 130A, after irradiation (and development, where required), includes an entrance pattern or mark 182A, two corresponding exit patterns or marks 182B, 182C, and two reference indicia images 162 (from reference indicia 160 on the phantom 100). The dosimeter sheet 130A also includes a dark shadow line mark 188 (shown as being horizontal in this view) that results from the interaction of radiation from the radiation beams with the inner planar member 125B illustrated in FIGS. 1-4.

With reference to FIGS. 5 and 7, the entrance mark 182A in FIG. 7 results from a radiation beam at position P1 entering the entrance zone 172A (FIG. 5). The exit mark 182B results from a radiation beam at position P2 exiting the phantom device 100 at the exit zone 174B illustrated in FIG. 5. The exit mark 182C in FIG. 5 results from a radiation beam at position P3 exiting the phantom device 100 at the exit zone 174C as illustrated in FIG. 5. The reference indicia marks 162 shown in FIG. 7 result from the reference indicia 160 provided by the phantom 100 (shown with hook 162h and with the center digitally connected to define the image registration).

It should be understood that corresponding entrance and exit marks similar to those shown in FIG. 5 may be formed on dosimeter sheets 130B and 130C. Thus, the beam trajectory direction 170 of the radiation beam in position P1 may be determined based on the location of the entrance mark 182A (FIG. 7) in the entrance zone 172A and the exit marks formed by the same radiation beam in position P1 on dosimeter sheets 130B and 130C at the exit zone 174A. Similar beam trajectories from beam positions P2 and P3 can be determined from entrance and exit marks on the dosimeter sheets 130A, 130B and 130C, and the intersection between the beam trajectories, or isocenter, can be determined. Because the size of the phantom is known and the orientation (what side is where) is known from the reference indicia, reference location coordinates can be used to automatically identify and define a coordinate system with respect to the phantom device 100 so that the isocenter can be identified in the radiation treatment device.

Figure 8:
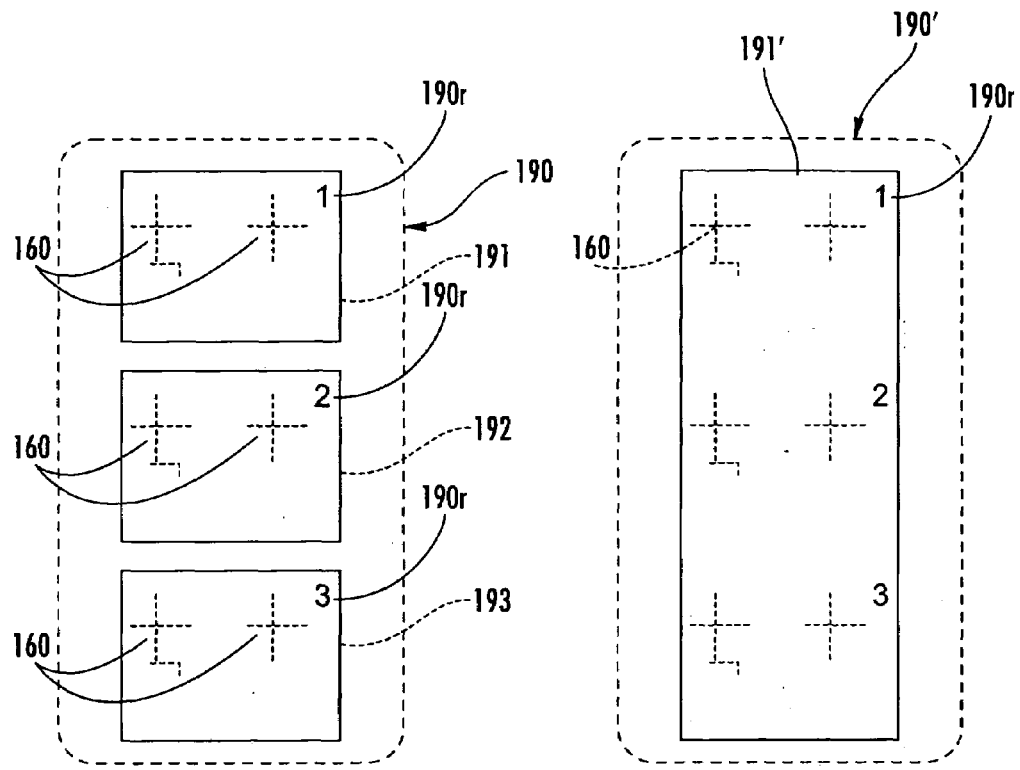
FIG. 8A is a schematic illustration of a kit of dosimeter sheets for use with a phantom according to embodiments of the present invention.
FIG. 8B is a schematic illustration of another embodiment of a dosimeter sheet for use with a phantom according to embodiments of the present invention.

In some embodiments, as shown in FIG. 8A, a kit 190 is provided including a plurality of radiation sensitive dosimeter sheets 191, 192, 193 that are sized and configured to fit on target (typically primary) surfaces of the phantom device 100. The radiation sensitive dosimeter sheets may optionally include visual markings or indicia 190r that identify the position of each sheet with respect to a phantom device (shown as sheets 1, 2 and 3 that correspond to sides 1, 2 and 3 which may be marked on the phantom body). In other embodiments, the sheets 191, 192, 193 may be configured so that they will be visually matched such as about a perimeter portion thereof (so as not to inhibit radiation exposure) to mount to a select, similarly colored or patterned side, and/or to only attach to a proper side.

In some embodiments, dosimeter sheets may be provided with markings that correspond to the phantom device 100 surfaces 110A, 110B and 110C. A technician can attach (position the dosimeter sheets in or on the) to respective surfaces 110A, 10B and 110C that may be configured with sides 1, 2, 3, etc.

Alternatively, as shown in FIG. 8B, the kit 190 can include a single dosimeter sheet 191' that is configured to mount to the phantom 100. As for the multiple sheet embodiment, the sheet 191' may include reference markings 160 and/or placement identifiers to assist in operator placement.

Figure 9:
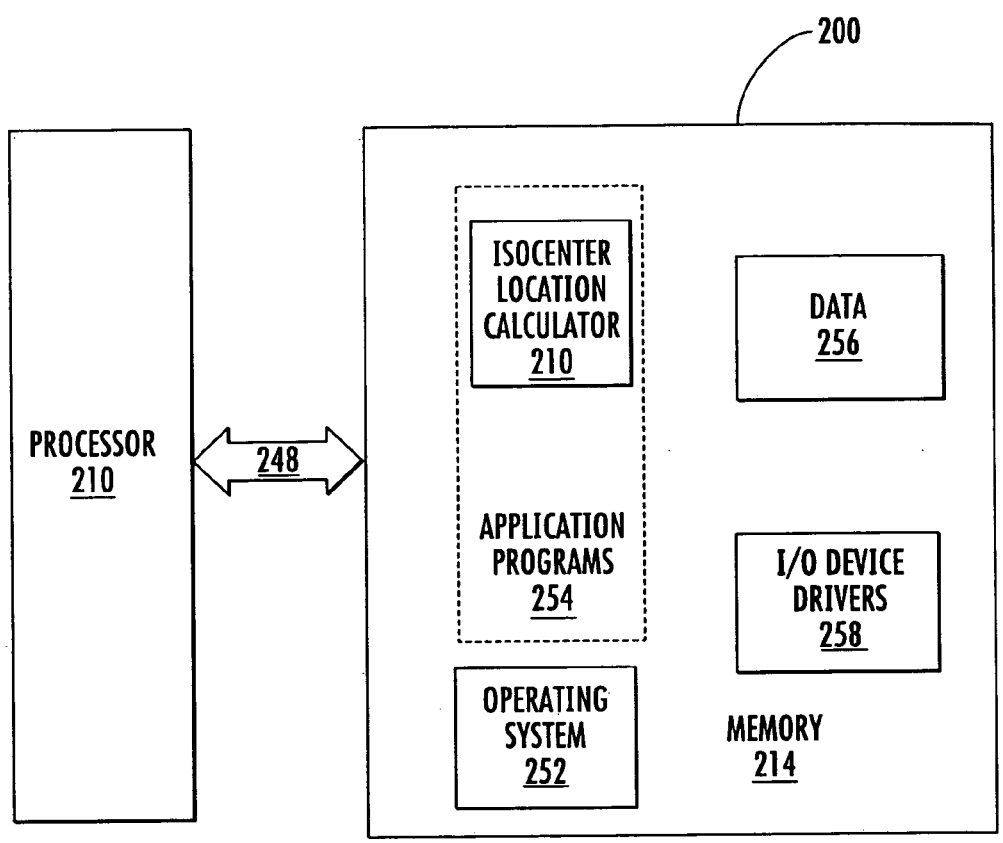
FIG. 9 is a schematic diagram of data processing systems according to embodiments of the present invention.
Figure 10:
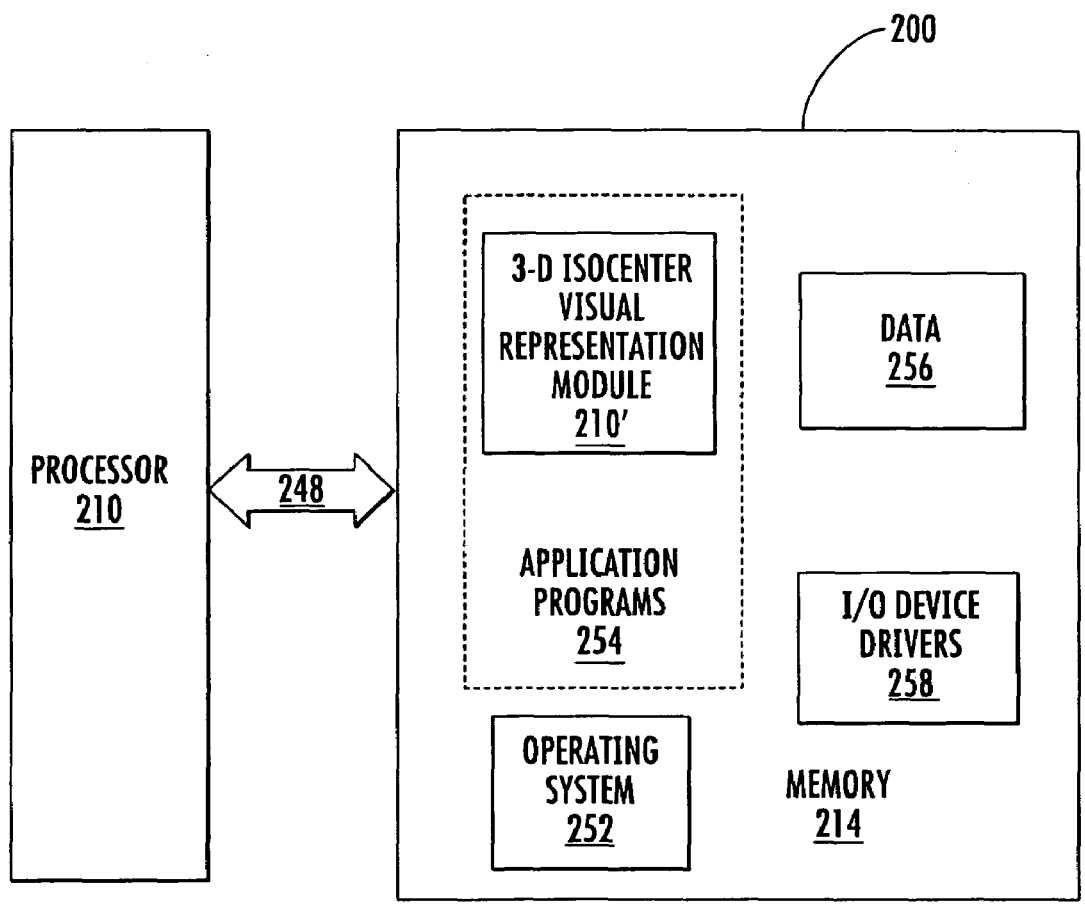
FIG. 10 is a schematic diagram of 3-D isocenter visualization data processing systems according to embodiments of the present invention.

The isocenter location calculator 210 in FIG. 9 and/or the virtual 3-D visualization module 210' in FIG. 10 may be configured to electronically recognize the digitized markings that identify the position of each sheet with respect to the phantom device 100. Accordingly, the data from the dosimeter sheets 191, 192, 193 may be automatically analyzed using the isocenter location calculator 210 and/or visualization module 210'.

In some embodiments, as shown, the sheets 191, 192, and 193 may be pre-configured with reference indicia 160 thereby reducing the number of radiation exposure steps during the calibration or quality assurance procedure. Computer software can be used to programmatically determine the intersection point between two or more beam trajectories, for example, as described with respect to FIGS. 9 and 10. Examples of commercially available imaging software that may be used to analyze the images from the dosimeter sheets 130A, 130B and 130C include ImageJ™.

The device 100 may be positioned in a desired radiation treatment system location using positioning techniques known to those of skill in the art, such as by using computer tomography (CT) imaging (slit and fan-beam), ultrasound imaging, magnetic resonance imaging (MRI) imaging, X-ray imaging, portal imaging, or other medical images for IGRT, or laser guided techniques. As illustrated, the center marker 150 is configured so that it is visible when a particular imaging and/or positioning technique is used. For example, the marker 150 can be radiopaque so that it may be visible on an imaging scan, such as for example, CT scans. Radiopaque materials are well-known and include dense metals, such as steel, lead or tungsten. However, it should be understood that non-radiopaque markers may also be used, for example, if a positioning technique is selected that does not require radiopaque characteristics, such as a laser guided technique or MRI.

The position of the marker 150 in a coordinate system defined by the indicia 160 may be measured or held at a location with a predetermined known value. After the marker 150 is positioned in the estimated isocenter of a radiation treatment device, radiation beams can be applied to the device 100 at positions P1, P2 and/or P3 as illustrated in FIG. 5 to determine the isocenter of the radiation treatment device. For example, the radiation beams at positions P1, P2 and/or P3 can irradiate the dosimeter sheets 130A, 130B and/or 130C. The dosimeter sheets 130A, 130B and/or 130C can be removed from the phantom device 100 and developed, and the entrance and exit marks from the beams can be used to determine an intersection point. The intersection point between the radiation beam trajectories can be compared to the estimated isocenter, that is, the position of the marker 150. Accordingly, the positioning techniques used to position the marker 150 in the estimated isocenter may be evaluated based on a possible difference between the intersection point of the beam trajectories and the position of the marker 150. If the intersection point of the beam trajectories and the position of the marker 150 are the same, the positioning technique used to position the marker 150 at the isocenter can be verified.

As illustrated, the device 100 provides three spaced apart opposed surfaces, i.e., faces 110A, 110B and 110C, such that a radiation beam trajectory passes through at lease two of the opposed surfaces, for example, to define a beam trajectory as described above. As illustrated in FIG. 5, the surface of the dosimeter sheets 130A, 130B and 130C at the entrance zones 172A, 172B and 172C are not parallel to the surfaces of the respective exit zones 174A, 174B and 174C. In this configuration, as illustrated in FIGS. 6 and 7, the entrance mark 182A and the exit marks 182B and 182C on one of the dosimeter sheets 130A are off-angle so that the entrance mark 182A and the exit marks 182B and 182C may be easily differentiated from one another. That is, the entrance mark 182A is generally centered in the dosimeter sheet 130A and the exit marks 182B and 192C are, respectively, to the left or right of the edge of the dosimeter sheet 130A. The lines associated with different selected marks (such as 182B and 182C, respectively in FIG. 7) can be electronically projected and extended in free space to determine the points of intersection.

As shown in FIGS. 1-5, the three faces 110A, 110B and 110C of the device 100 are substantially perpendicular to a common plane, i.e., the plane parallel to optional planar members 125A, 125B and 125C. As shown in FIG. 5, the cross sectional area through the common plane is an equilateral triangle. In this configuration, the dosimeter sheets 130A, 130B and 130C are substantially symmetric with respect to one another so that the entrance and exit marks on dosimeter sheets 130B and 130C would be in approximately the same location as the entrance mark 182A and the exit marks 182B and 182C as shown on dosimeter sheet 130A in FIGS. 6 and 7.

Although the dosimeter sheets 130A, 130B and 130C are illustrated as three separate sheets, it should be understood that a single sheet that is held by the three faces 110A, 110B and 10C may be used.

In some other embodiments, lasers or other location defining components can be mounted to or aligned with the phantom 100 to evaluate the system isocenter. For example, lasers can be operated to generate a visible projected estimated radiation isocenter of treatment based on the position of the radiation source, collimator, gantry and/or patient table. The phantom 100 can be placed in the visually projected center of treatment so that the center of the phantom (using center reference 150) is aligned with the estimated light defined center of treatment. The isocenter evaluation radiation beams 180 (at P1-P3, FIG. 5) can be generated from the desired positions and the dosimeter sheets imaged and digitized. The accuracy of the isocenter location system can be verified or the deviation noted for proper adjustment or calibration.

FIGS. 9 and 10 are block diagrams of exemplary embodiments of data processing systems that illustrate systems, methods, and computer program products in accordance with embodiments of the present invention. The data processing systems can be provided in a computer useable medium as computer readable (meaning computer useable) program code. As illustrated in FIGS. 9 and 10, a processor 210 communicates with a memory 214 via an address/data bus 248. The processor 210 can be any commercially available or custom microprocessor. The memory 214 is representative of the overall hierarchy of memory devices containing the software and data used to implement the functionality of the data processing system 200. The memory 214 can include, but is not limited to, the following types of devices: cache, ROM, PROM, EPROM, EEPROM, flash memory, SRAM, and DRAM.

The memory 214 may include several categories of software and data used in the data processing system 200: an operating system 252; application programs 254; input/output (I/O) device drivers 258; and data 256. As shown in FIG. 9, the application programs 254 can include an isocenter location calculator 210. In certain embodiments, the isocenter location calculator 210 includes computer program code for calculating the isocenter location with respect to the phantom device 100. As shown in FIG. 10, the application programs 254 can include a virtual radiation isocenter 3-D visualization module that visually represents isocenter measurement deviations.

The data 256 may include image data obtained from a dosimeter sheet, such as dosimeter sheets 130A, 130B and 130C in FIG. 5. The dosimeter sheets can be scanned and entered into data 256 of the data processing system 200 in FIGS. 9 and/or 10. The isocenter location calculator 210 may include computer readable code that calculates various locations, such as the isocenter of the radiation treatment device, from known or measured values and/or date from the dosimeter sheets.

For example, with reference to FIG. 7, the isocenter location calculator 210 may analyze the image of the dosimeter sheet 130A to determine the locations of the entrance mark 182A and the exit marks 182B and 182C. The isocenter location calculator 210 can fit a line to the entrance mark 182A and the exit marks 182B and 182, for example, by using data points 186 and conventional line fitting techniques known to those of skill in the art. The isocenter location calculator 210 can use the positions of the reference location coordinates 162 to define a coordinate system with respect to the phantom device 100 (shown in FIGS. 1-5).

The coordinate system used to measure radiation isocenter position and/or phantom position in 3-D (and deviation) according to embodiments of the present invention is typically a Cartesian coordinate system but a cylindrical or spherical (polar) coordinate system may also be used.

As will be appreciated by those of skill in the art, the operating system 252 may be any operating system suitable for use with a data processing system, such as OS/2, AIX, OS/390 or System390 from International Business Machines Corporation, Armonk, N.Y., Windows CE, Windows NT, Windows95, Windows98, Windows XP or Windows2000 from Microsoft Corporation, Redmond, Wash., Unix or Linux or FreeBSD, Palm OS from Palm, Inc., Mac OS from Apple Computer, or proprietary operating systems. The I/O device drivers 258 typically include software routines accessed through the operating system 252 by the application programs 254 to communicate with devices such as I/O data port(s), data storage 256 and certain memory 214 components and/or the distance measurement device 225. The application programs 254 are illustrative of the programs that implement the various features of the data processing system 200 and preferably include at least one application which supports operations according to embodiments of the present invention. The data 256 represents the static and dynamic data used by the application programs 254, the operating system 252, the I/O device drivers 258, and other software programs that may reside in the memory 214.

Although the present invention is illustrated, for example, with reference to the isocenter location calculator 210 or visualization module 210' being an application program in FIG. 9 or 10, as will be appreciated by those of skill in the art, other configurations may also be utilized while still benefiting from the teachings of the present invention. For example, the isocenter location calculator 210 may also be incorporated into the operating system 252, the I/O device drivers 258 or other such logical division of the data processing system 200. Thus, the present invention should not be construed as limited to the configurations of FIGS. 9, 10, which is intended to encompass any configuration capable of carrying out the operations described herein.

The isocenter location calculator 210 can be used to analyze digitized data from a dosimeter sheet. For example, the isocenter location calculator 210 identify or calculate the location of the entrance mark 182A and the exit marks 182B and 182C as shown in FIG. 7, for example, using line-fitting techniques, to determine the intersection and/or center of the "cross" shaped beam. The isocenter location calculator 210 can identify beam trajectories based on the entrance and/or exit marks. The isocenter location calculator 210 can identify or calculate the position of the intersection of the beam trajectories to estimate an isocenter for a radiation treatment device, for example, with respect to a reference coordinate (such as the reference coordinates 162 in FIG. 7) included in the data from the dosimeter sheets. The isocenter location calculator 210 can compare the isocenter to a previously estimated isocenter to evaluate or confirm the isocenter and/or positioning techniques.

The I/O data port can be used to transfer information between the data processing system 200 another computer system or a network either a local and/or global network (e.g., the Internet), such as a scanning device for scanning the images from the dosimeter sheets, or to other devices controlled by the processor. These components may be conventional components such as those used in many conventional data processing systems that may be configured in accordance with the present invention to operate as described herein.

While the present invention is illustrated, for example, with reference to particular divisions of programs, functions and memories, the present invention should not be construed as limited to such logical divisions. Thus, the present invention should not be construed as limited to the configuration of FIGS. 9 and 10 but is intended to encompass any configuration capable of carrying out the operations described herein.

The flowcharts and block diagrams of certain of the figures herein illustrate the architecture, functionality, and operation of possible implementations of embodiments of the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order, depending upon the functionality involved.

In some embodiments, to calculate the "true" isocenter, the known geometric center of the 3-D phantom can be used as a known point in space. In some embodiments, the centroid or other known location relative to the shape of the phantom, rather than and/or in combination with, the center of the 3-D phantom can be used. The space or region where the lines from intersecting "test" beams cross in space can be determined using the irradiation patterns from three sides of the phantom. This space or point can be calculated and compared to the phantom center to provide a system measure of error or offset in three-dimensions to confirm or evaluate if the system isocenter is offset from what is believed to be the true isocenter. In some embodiments, the measurement can be determined in better than about a sub-millimeter measurement accuracy.

Figure 11:
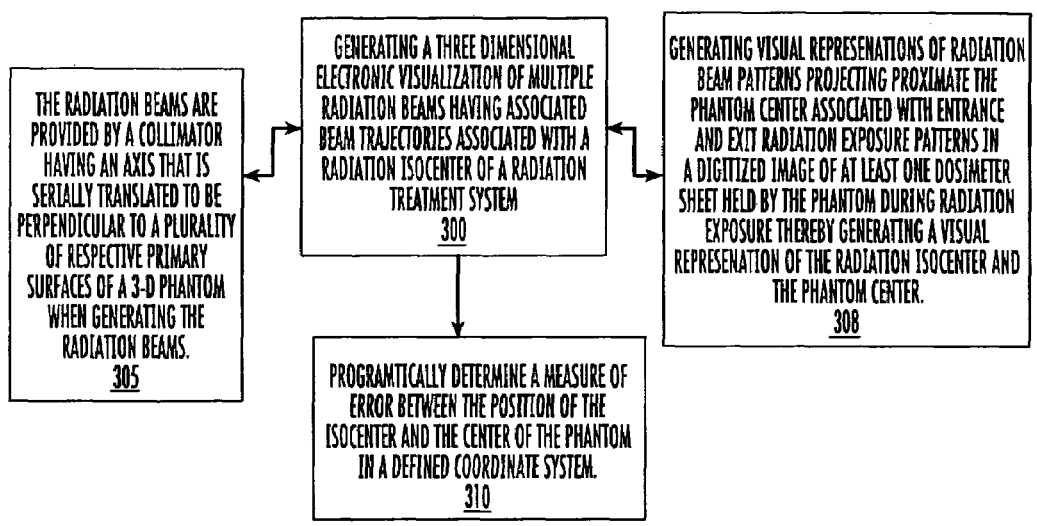
FIG. 11 is a flow chart of exemplary operations that can be used to carry out methods of the present invention.

FIG. 11 is a flow chart of exemplary operations that can be used to visualize the deviation from an estimated center of the system radiation isocenter. As shown, a three dimensional electronic visualization of multiple radiation beams having associated beam trajectories for determining a radiation isocenter of a radiation treatment system can be generated (block 300). A measure of error between the estimated isocenter and the center of the phantom can be programmatically determined in a defined coordinate system (block 310).

The radiation beams can be provided by a collimator that has an axis that is serially translated to be generally perpendicular (or at a desired angular offset) to a plurality of respective primary surfaces of a 3-D phantom when generating the radiation beams (block 305). As such, the collimator may be perpendicular to the phantom surface (a typically configuration) or may be positioned so that the beam may pass through at an angle. Visual radiation beam patterns (typically comprising a plurality of intersecting lines) that are projected through the phantom center based on entrance and exit radiation exposure patterns associated with irradiation exposure of the test beams in a digitized image of irradiation exposure of radiation sensitive media (such as at least one dosimeter sheet or CCD) can be generated thereby generating a visual representation of the radiation isocenter and phantom center (block 308).

Figure 12:
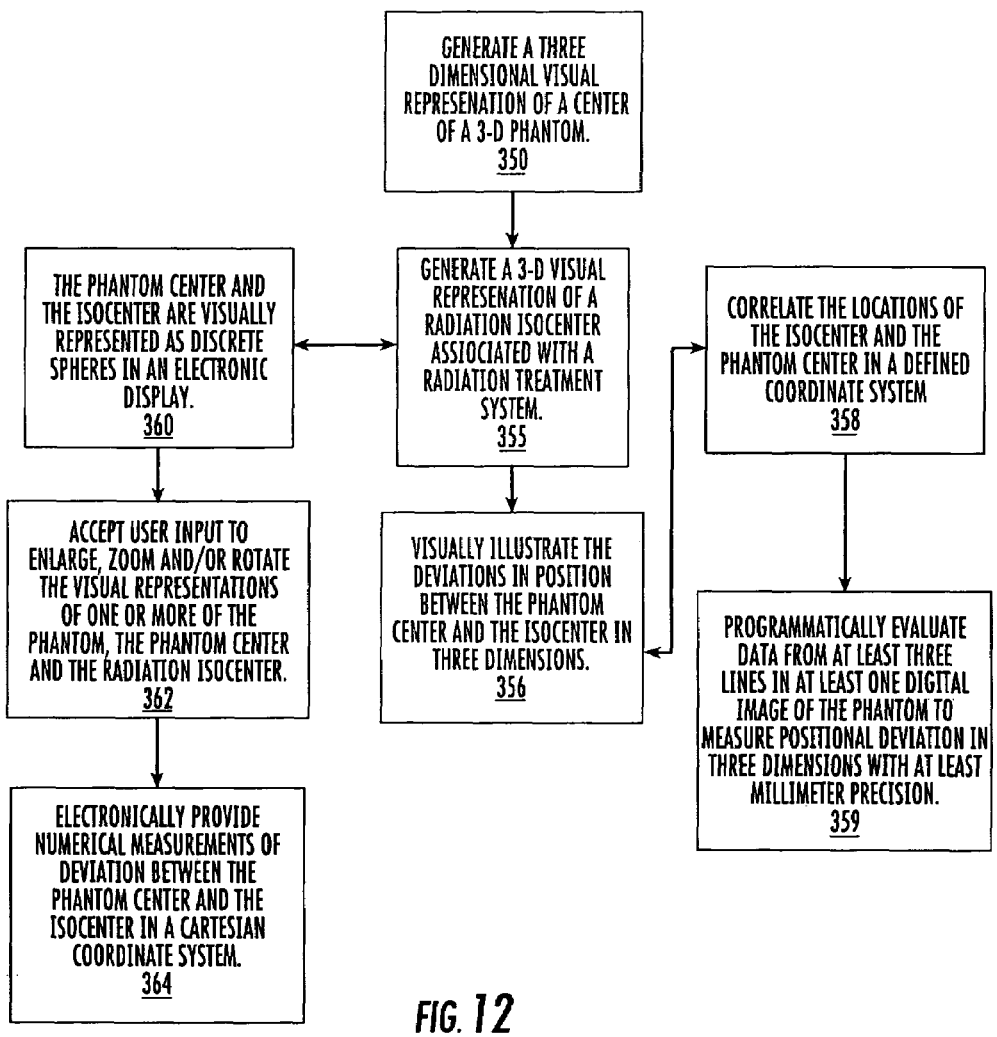
FIG. 12 is a flow chart of exemplary operations that can be used to carry out methods of the present invention.

FIG. 12 is a flow chart of some exemplary operations that can be used to generate visual representations of the phantom and/or system radiation isocenter according to some embodiments of the present invention. As shown, a three-dimensional visual representation of a center of a 3-D phantom can be generated (block 350). A 3-D representation of a radiation isocenter associated with a radiation system can be generated (block 355). The deviations between the position of the phantom center in free space and the system isocenter in free space can be visually illustrated in 3-D (block 356).

The locations of the isocenter and the phantom center can be correlated to a defined coordinate system (block 358). The data from at least three lines in a digital image of the phantom can be programmatically evaluated to measure the size of deviation in three dimensions relatively precisely, such as within mm precision, and typically with about sub-millimeter precision or better (block 359).

In particular embodiments, the phantom center and the system isocenter can be visually represented as discrete spheres in an electronic display (block 360). User input can be accepted to enlarge, zoom and/or rotate the visualization including the phantom center and isocenter (block 362). Numerical measurements of offset and/or deviation between the phantom center and the isocenter can be provided in three dimensions in a Cartesian coordinate system (block 364).

Figure 13:
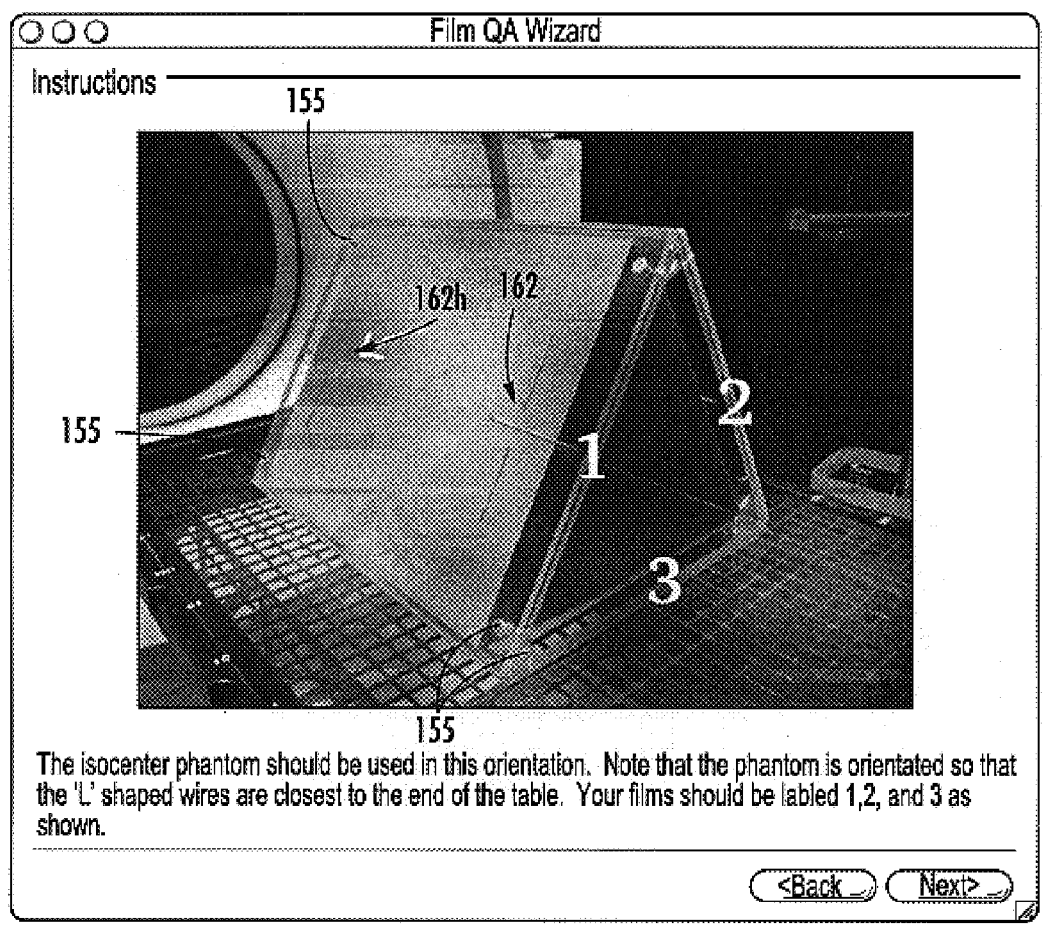
FIG. 13 is a perspective view of a 3-D phantom in a use orientation according to embodiments of the present invention.

FIG. 13 is a perspective view of the isocenter phantom 100 shown in position on a patient table. Each side of the phantom 100 is numbered as 1, 2 or 3, respectively. The phantom is oriented on the table so that the "L" shaped reference indicia or fiducial marker 162 h rather than the elongate reference indicia or fiducial marker 162 is oriented toward the forward end of the table. This allows for the computer algorithm to have a consistent orientation for calculations. However, an arbitrary orientation can be used and the image recognition software can be programmed to automatically identify the orientation of the phantom (and dosimeter or radiation-sensitive image media) used to obtain the test radiation exposure images.

Figure 14:
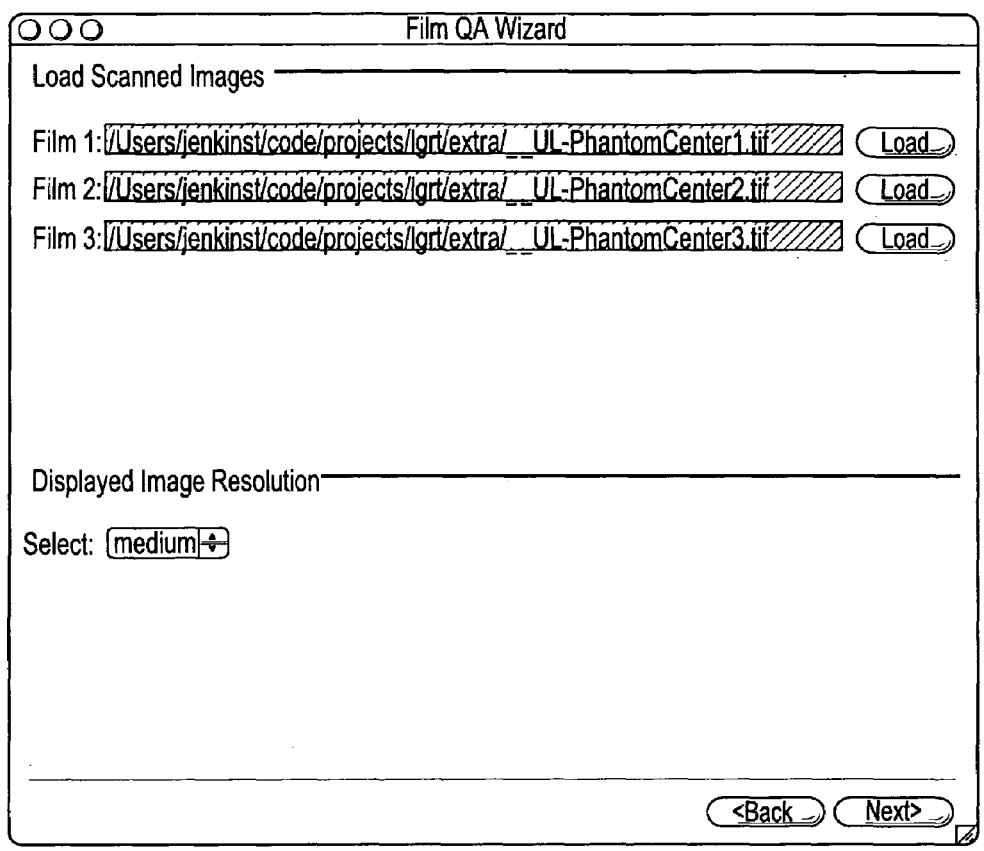
FIG. 14 is a screen shot of an example of a set of three related digitized phantom phantom based radiation images according to embodiments of the present invention.
Figure 15:
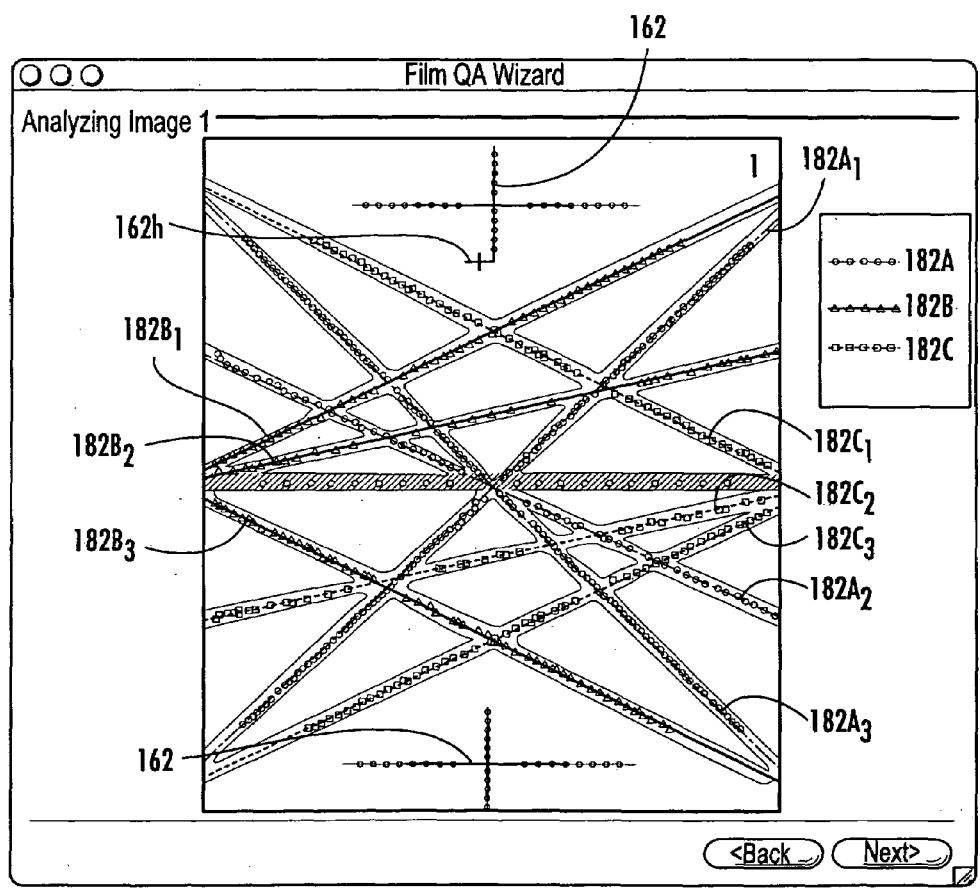
FIGS. 15-17 are screen shots of digitized radiation pattern images relative to sides 1-3 of the phantom according to embodiments of the present invention.
Figure 16:
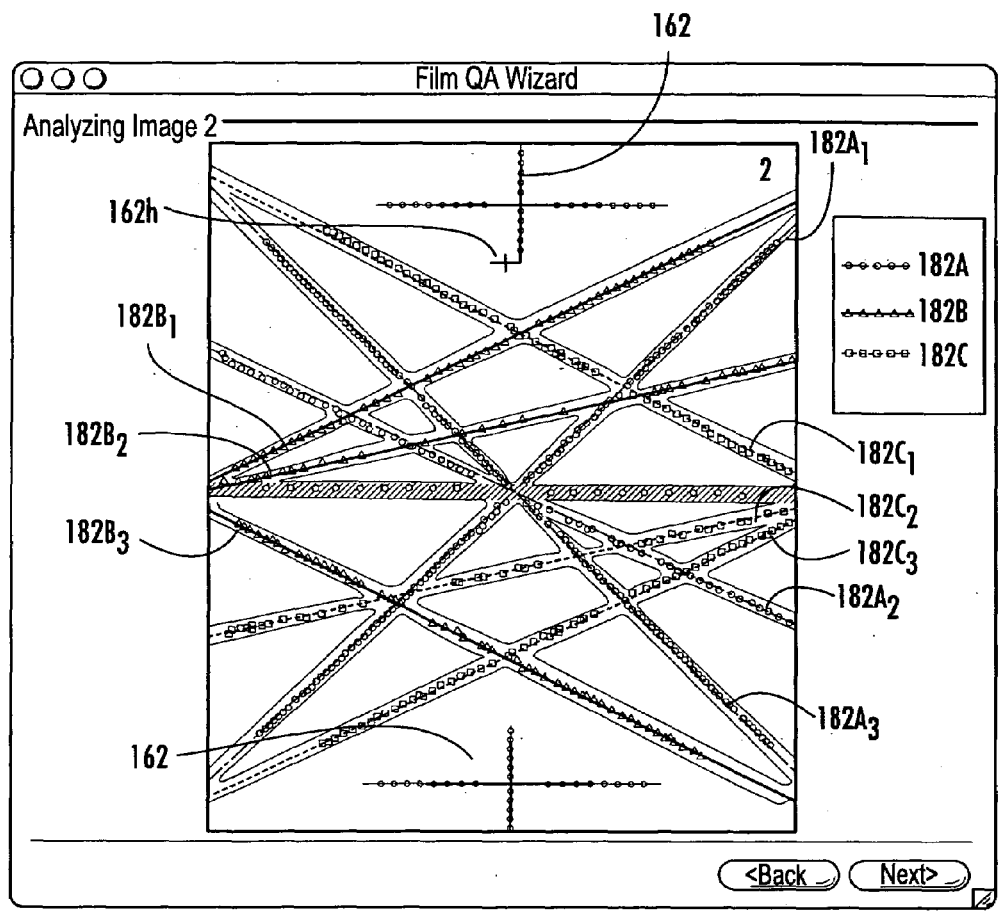
Figure 17:
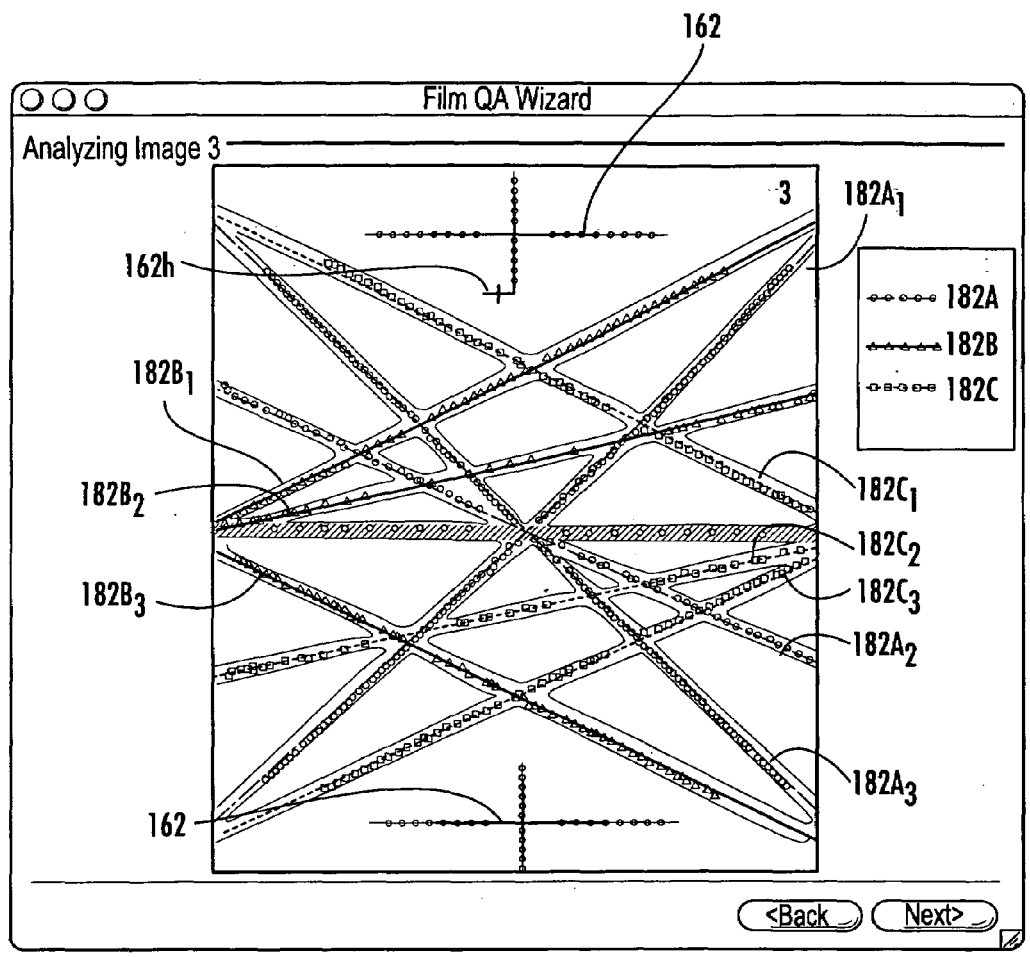

FIG. 14 is a screen shot of three different digitized images, of three different respective sides of the phantom, forming an image set. The image set can be manually correlated or selected for further analysis or electronically indexed or otherwise correlated or recognized. FIGS. 15-17 illustrate that the system can be configured to generate lines for each side of interest of the phantom that correspond to the developed irradiation pattern lines, one for an entry pattern 182A, shown as having three associated intersecting lines (crossing generally medially in FIGS. 15-17), one for two corresponding exit patterns, one for exiting side 3 (182B1, 182B2, 182B3) and one for exiting side 2 (182C1, 182C2, 182C3). The intersecting points for each of the exit patterns occurs off the image sheet and is projected and can be calculated based on coordinates and/or a slope of the associated lines. In operation, the system can be configured to automatically find the registration marks of the side and properly orient the side using a known scale and pixel sizes. The system can then define the entry line(s) (shown as three lines in an intersecting or general "X" pattern) and exit lines (also three lines in a general "X" pattern). The system can use locational and position data on the lines in each side to measure a size of offset in three dimensions.

The following exemplary three code sequences are provided to illustrate an example of how coordinates can be converted between two-dimensional space (of the digitized images) to three-dimensional space (to generate a three dimensional image). Although provided in JAVA, other programming languages and/or sequences may be employed.

CODE SNIPPET 1:
This piece of code is responsible for determining the coordinates of each corner of the digitized film images in the 3D space used to draw the final phantom schematic. It depends on code snippets 2 & 3 for part of the calculation.

```
    private Point3d[ ] getFilmCoordinates(int num)
    {
        FilmQaAnalysisPanel p = null;
        switch(num)
        { case 1: p = m_wizard.m_analysisPanel1; break;
            case 2: p = m_wizard.m_analysisPanel2; break;
            case 3: p = m_wizard.m_analysisPanel3; break;
        }
        // get the points in fluence space
        double xMin = p.m_fluenceData.getMinX( );
        double xMax = p.m_fluenceData.getMaxX( );
        double yMin = p.m_fluenceData.getMinY( );
        double yMax = p.m_fluenceData.getMaxY( );
        Point3d pt1 = new Point3d(xMin, yMin, 0d);
        Point3d pt2 = new Point3d(xMax, yMin, 0d);
        Point3d pt3 = new Point3d(xMax, yMax, 0d);
        Point3d pt4 = new Point3d(xMin, yMax, 0d);
        // convert the points into the registered coordinate system; the origin is
        // halfway between the wire markers, x is to the right, and y is towards
        // the top; the "L" tick should be towards the left
        Transform3D t3d = p.getRegistrationTransform( );
        t3d.transform(pt1);
        t3d.transform(pt2);
        t3d.transform(pt3);
        t3d.transform(pt4);
        // now convert from registered space into the phantom coordinate system
        t3d = FilmQawizard.getPanelTransform(num);
        t3d.transform(pt1);
        t3d.transform(pt2);
        t3d.transform(pt3);
        t3d.transform(pt4);
        return new Point3d[ ] {pt1, pt2, pt3, pt4};
    }
```
CODE SNIPPET 2:
```
    /**
     * Provides a tranform from fluence space into registered coordinate system. This
     * system has its origin in the middle of the film, half way between the two
     * registration crosses. x is to the right and y is towards the
     'L' shaped
     * marker. The tip of the 'L' should point towards the left.
     */
    Transform3D getRegistrationTransform( )
    {
        // get the location of the registration crosses in registration space
        Point2d ptTopReg = FilmQaWizard.POINT1;
        Point2d ptBtmReg = FilmQaWizard.POINT2;
        assert(ptTopReg.x == ptBtmReg.x);
        // get the location of the registration crosses in fluence space
        Point3d ptTop = new Point3d(m_pt1CM.x, m_pt1CM.y, 0d);
        Point3d ptBtm = new Point3d(m_pt2CM.x, m_pt2CM.y, 0d);
        // calc the fluence mid point
        Point3d ptMid = new Point3d(ptTop);
        ptMid.add(ptBtm);
        ptMid.scale(0.5);
```

```
        //
        // find transform that converts from fluence space into
registration space
        //
        Transform3D t3d = new Transform3D( );
        // translation
        Vector3d vTrans = new Vector3d(ptMid);
        vTrans.negate( );
        Transform3D t3dTrans = new Transform3D( );
        t3dTrans.setTranslation(vTrans);
        t3d.mul(t3dTrans, t3d);
        t3dTrans.transform(ptTop);
        t3dTrans.transform(ptBtm);
        t3dTrans.transform(ptMid);
        // flip the y axis
        Transform3D t3dFlipY = new Transform3D( );
        t3dFlipY.rotX(Math.PI);
        t3d.mul(t3dFlipY, t3d);
        t3dFlipY.transform(ptTop);
        t3dFlipY.transform(ptBtm);
        t3dFlipY.transform(ptMid);
        // scale
        double scale = ptTopReg.distance(ptBtmReg) /
ptTop.distance(ptBtm);
        Transform3D t3dScale = new Transform3D( );
        t3dScale.setScale(scale);
        t3d.mul(t3dScale, t3d);
        t3dScale.transform(ptTop);
        t3dScale.transform(ptBtm);
        t3dScale.transform(ptMid);
        // rotation
        Vector3d vReg = new Vector3d(
            ptBtmReg.x - ptTopReg.x,
            ptBtmReg.y - ptTopReg.y,
            0d);
        Vector3d vFlu = new Vector3d(
            ptBtm.x - ptTop.x,
            ptBtm.y - ptTop.y,
            0d);
        double angle = vReg.angle(vFlu);
        Vector3d vNormal = new Vector3d( );
        vNormal.cross(vReg, vFlu);
        if(vNormal.z > 0) angle *= -1;
        Transform3D t3dRot = new Transform3D( );
        t3dRot.rotZ(angle);
        t3d.mul(t3dRot, t3d);
        t3dRot.transform(ptTop);
        t3dRot.transform(ptBtm);
        t3dRot.transform(ptMid);
        // adjust for improper film orientation
        if(m_tickLocation == FilmQaWizard.
        TICK_IN_UPPER_RIGHT ||
            m_tickLocation == FilmQaWizard.
            TICK_IN_LOWER_RIGHT)
        {
            Transform3D t3dFlipX = new Transform3D( );
            t3dFlipX.rotY(Math.PI);
            t3d.mul(t3dFlipX, t3d);
        }
        if(m_tickLocation == FilmQaWizard.
        TICK_IN_LOWER_LEFT ||
            m_tickLocation == FilmQaWizard.
            TICK_IN_LOWER_RIGHT)
        {
            t3d.mul(t3dFlipY, t3d);
        }
        // the final, combined tranform
        return t3d;
    }
CODE SNIPPET 3:
    /**
        * Creates a Transform3D that will convert from registered panel
coordinates
        * into phantom coordinates where the BB is at the origin and x
points to the
        * right side of the phantom and y points towards the top
triangular face of
        * the phantom. Z points towards the gantry in its normal,
upright position.
        *
        * @param panel selects panel 1, 2, or 3
        * @return Transform3D
        */
    static Transform3D getPanelTransform(int panel)
    {
        Transform3D t3d = new Transform3D( );
        // calc distance from BB to outer face of the phantom
        double r = 0.5 * PHANTOM_EDGE_LENGTH_CM *
        Math.tan(Math.toRadians
(30.0));
        // account for half the thickness of a ready pak
        r += READY_PAK_THICKNESS_CM / 2d;
        // translate the panel by this amount
        Vector3d vTrans = new Vector3d(0d, 0d, r);
        Transform3D t3dTrans = new Transform3D( );
        t3dTrans.set(vTrans);
        t3d.mul(t3dTrans, t3d);
        // rotate panel into the proper orientation
        double angle = 0;
        switch(panel)
        {
            case 1: angle = Math.PI / -3d; break;
            case 2: angle = Math.PI / 3d; break;
            case 3: angle = Math.PI; break;
            // should never see this line
            default: assert false;
        }
        Transform3D t3dRot = new Transform3D( );
        t3dRot.rotY(angle);
        t3d.mul(t3dRot, t3d);
        // the final, combined transform
        return t3d;
    }
```

Figure 18A:
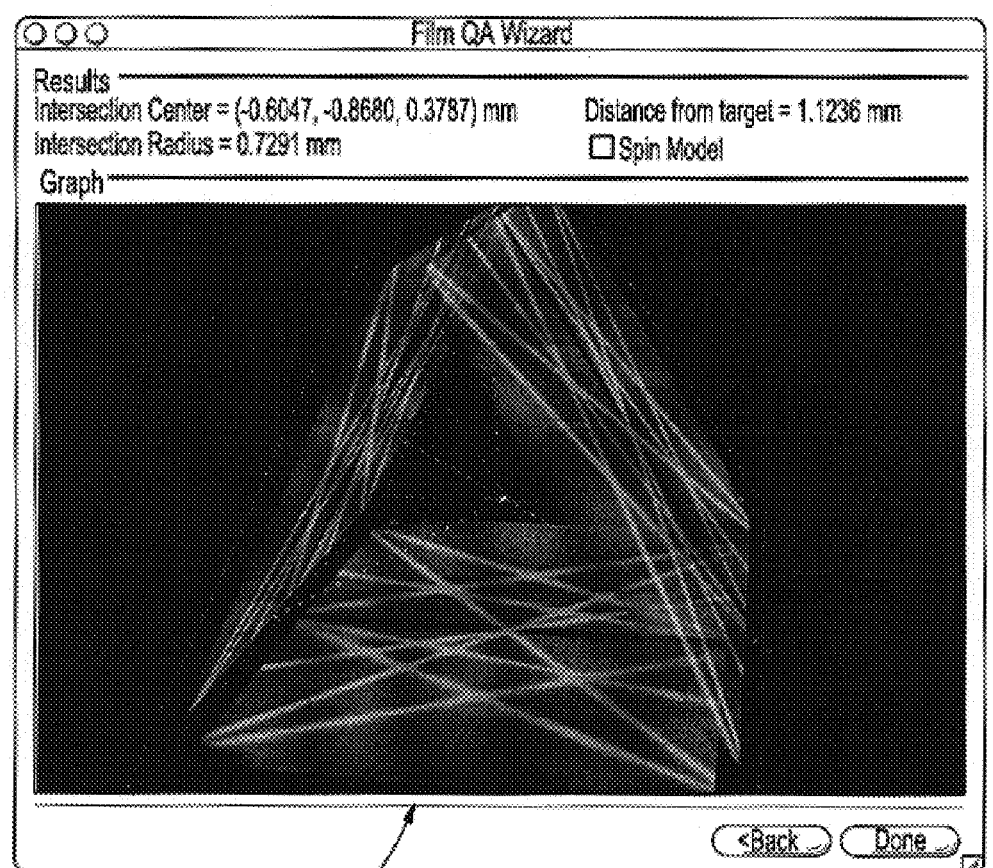
FIG. 18A is a three-dimensional virtual visualization of radiation patterns and center locations according to embodiments of the present invention.
Figure 18B:
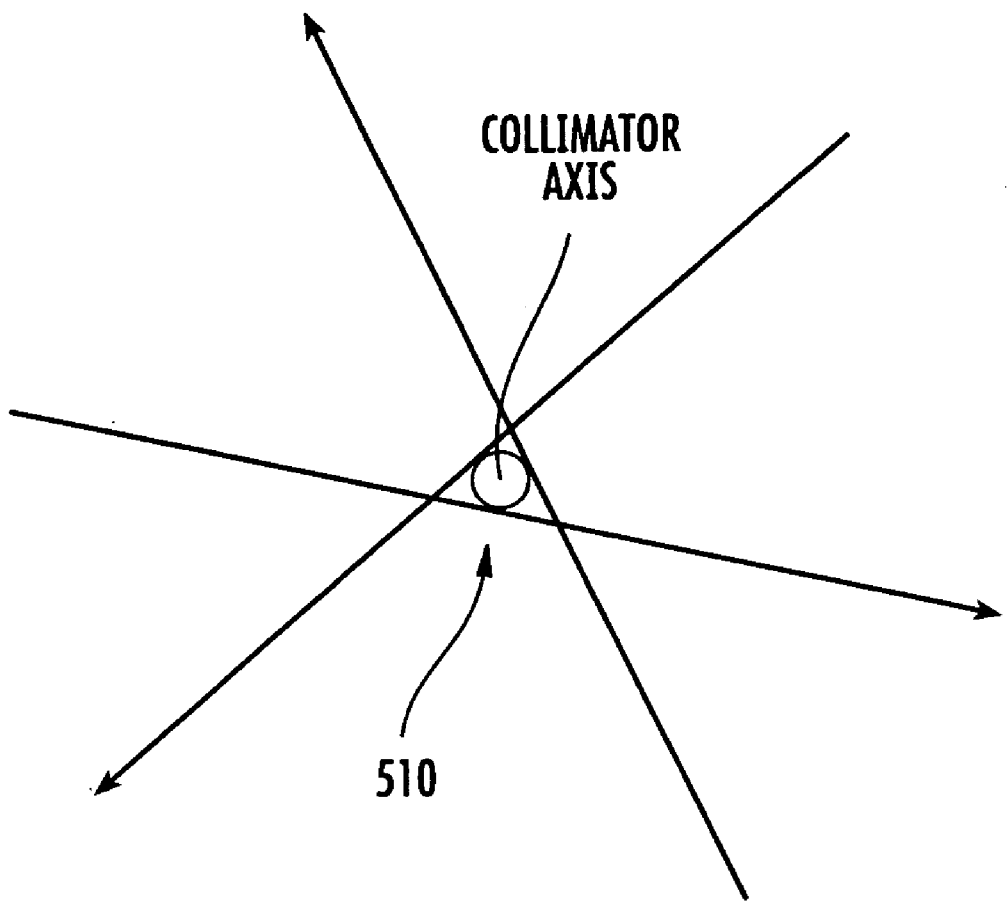
FIG. 18B is a schematic of a radiation pattern from a collimator axis that can generate a measurable small volume of mismatch or offset according to embodiments of the present invention.

FIG. 18A is a three dimensional visualization 500i of the phantom used to create a three-dimensional projection of the phantom center (shown by the small spot inside the phantom geometric body). FIG. 18B is a schematic illustration of radiation beams generated from different positions of the collimator axis that can generate a small volume of confusion 510 relative to the radiation isocenter, the volume of confusion defining the center offset when radiation is generated from three different positions (typically when moved relative to a fixed gantry position). Other system influences may also impact the location and variance or size of the radiation treatment isocenter (gantry, table, etc).

Figure 19:
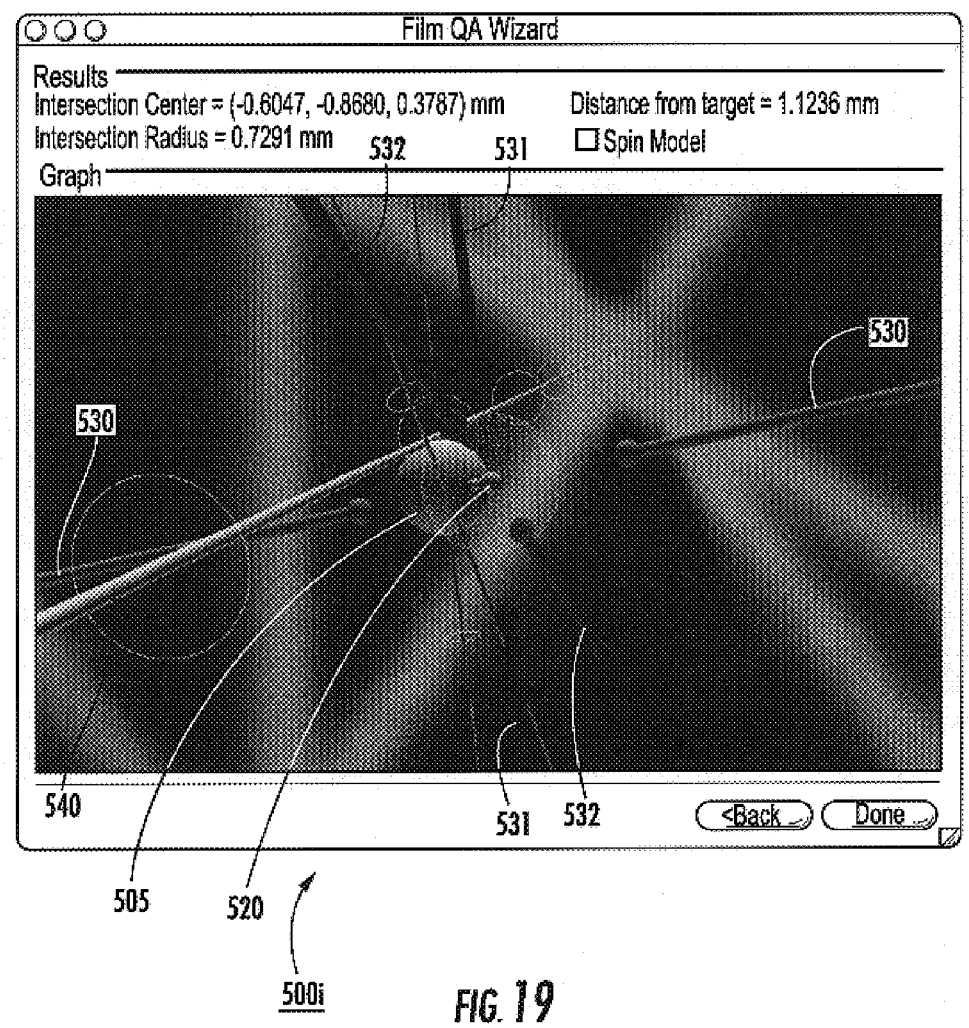
FIGS. 19-21 are screen shots of a 3-D radiation isocenter visualization images generated according to embodiments of the present invention.
Figure 20:
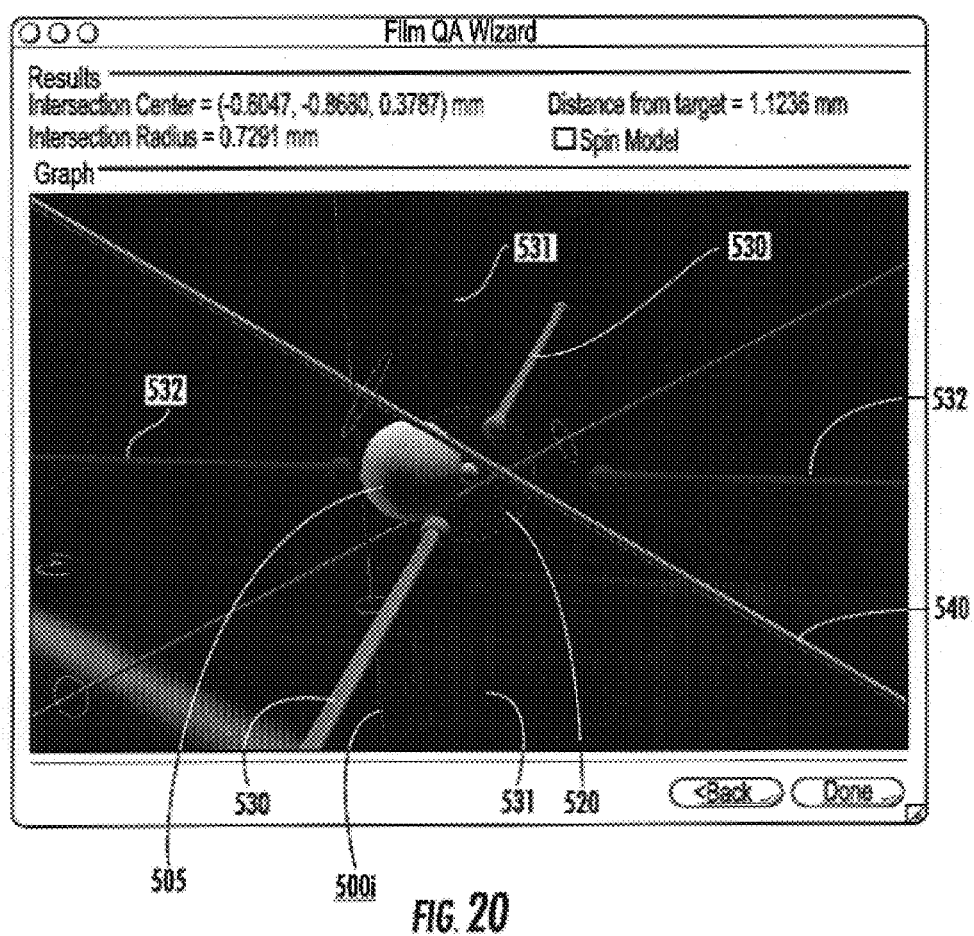
Figure 21:
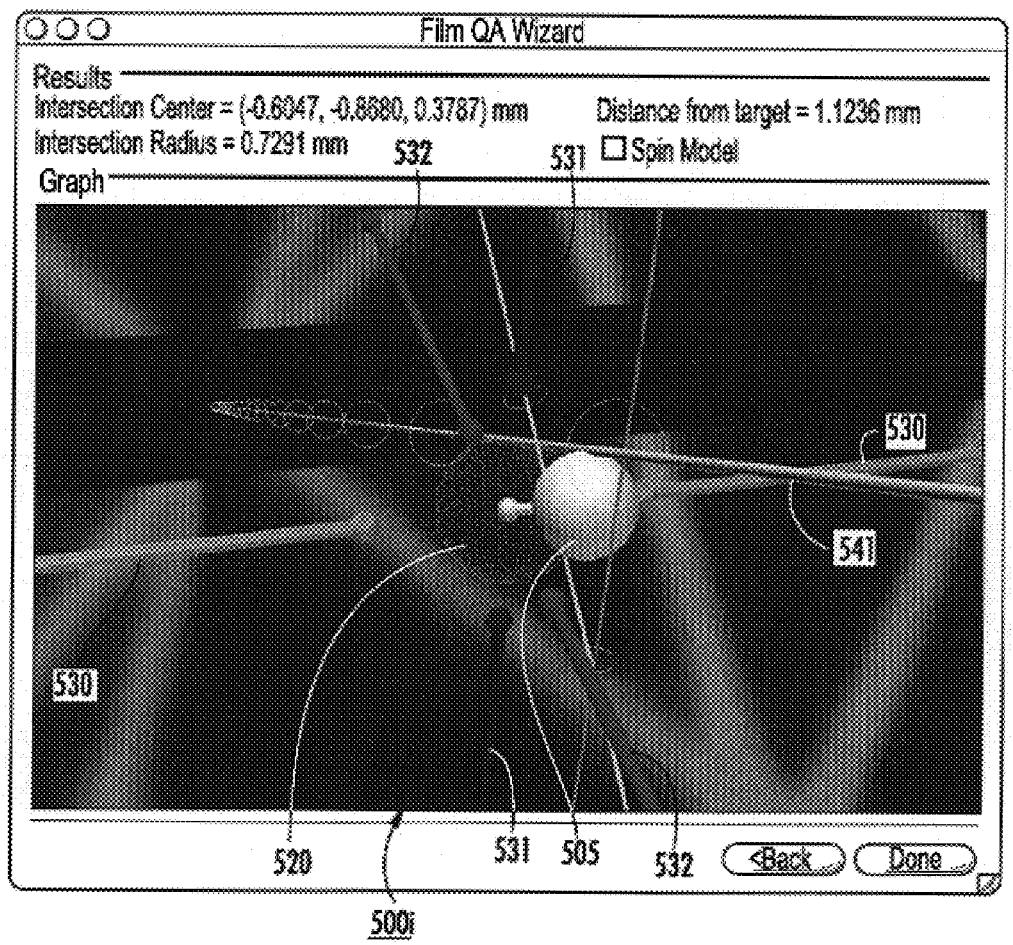

FIGS. 19-21 are electronically generated images 500i of the radiation isocenter shown relative to the phantom center, for quality assurance evaluation. The phantom geometric center is shown as the relatively large transparent sphere 520 and the measured radiation isocenter is shown by the smaller solid sphere 505. However, any desired shape or shapes, sizes and colors may be used to represent one or both centers. The location of the radiation isocenter 505 is defined in a known coordinate system (typically Cartesian) relative to the phantom center. As shown, the electronic isocenter evaluation can calculate that the radiation isocenter is located at position (−0.6047, −0.8680, 0.3787) mm, its offset (negative or positive) being relative to the location in space of the phantom center. In this example, the "Y" dimension provides the largest offset.

The system can be configured to illustrate radiation projections in each dimension. In the image 500i, lines can be drawn to represent the X, Y and Z axis of the phantom. As shown, line 530 corresponds to the Y dimension, line 531 corresponds to the Z dimension, and line 532 corresponds to the X dimension. As also shown, the rounded proximal ends are spaced at about 2 mm from the phantom center 520. As shown in FIG. 19, a rounded bar in the center of the geometric phantom center 520 can extend out to the measured isocenter 505. The length of the bar or line can change if the measured isocenter 505 is further or closer to the center of the geometric center 520.

The system isocenter can be calculated from the digitized radiation patterns generated by radiation projected from the different positions of the radiation source with respect to different sides of the phantom. As shown, the isocenter has a size that has a radius of 0.7291 mm (providing the size of the "isocenter" sphere). The three axes provide a measure of radiation isocenter, giving a center value and intersection, that can be calculated with sub-millimeter accuracy or better.

The multiple (three) elongate lines 540 crossing the phantom interior space tangential to the measured isocenter 505 in the screen shots represent the "collimator axis of rotation" or collimator positions. The collimator is the part of the linear accelerator that shapes the beam and is used to create the pattern on the film. The "gantry," on the other hand, is rotated to three positions to cause the collimator axis to cross the phantom from three different directions. The smallest sphere that touches the (yellow) elongate lines 540 represent the size and location of the radiation isocenter.

The view of the isocenter and phantom centers 505, 520, respectively, is shown at a distance from target of 1.1236 mm. The visualization system can be configured to accept user input to allow a user to "spin" the view to another angle, as well as to zoom (in or out), rotate or otherwise alter the 3-D image.

As shown in FIGS. 19-21, the irradiation images of different sides of the phantom, as well as the geometric shape of the phantom can be shown in the background (see side 3 reference mark shown in FIG. 20). However, selected features may be illustrated and other features removed as desired for a particular user or application.

Although discussed with respect to radiation isocenters, the above methodology may be used to calibrate laser positioning in radiation systems as well, see, for example, the discussion above regarding this embodiment.

The isocenter position evaluation can be carried out at any desired time, such as daily, upon set-up for respective patients and/or less frequently, such as monthly or after a maintenance procedure on the equipment.

In the drawings and specification, there have been disclosed exemplary embodiments of the invention and, although specific terms are employed, they are used in a generic and descriptive sense only and not for purposes of limitation, the scope of the invention being set forth in the following claims. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

What is claimed is:

1. A method of determining an isocenter location of a radiation treatment device, the method comprising:
   irradiating at least one radiation sensitive media on a three-dimensional phantom having a geometric shape with at least two opposed sides using a first radiation beam location having a first trajectory that passes through the two opposed surfaces at a first entrance position and a first exit position;
   irradiating the at least one radiation sensitive media using a second radiation beam location having a second trajectory that passes through the two opposed surfaces at a second entrance position and a second exit position; and
   programmatically determining an intersection between the first trajectory and the second trajectory to estimate an isocenter,
   wherein the radiation sensitive media comprises a generally planar film, the method further comprising positioning the at least one generally planar radiation sensitive film in or on a support member of a phantom assembly such that the film generally conforms to a shape defined by at least two opposed surfaces of the support member, wherein the first and second beams are configured to provide a beam pattern having plurality of lines with an intersecting location in the film, the method further comprising providing a reference indicia to the at least one film held by the support member to define at least one of a reference orientation, a geometric location identifier or a coordinate system with respect to the support member and film.

2. The method of claim 1, wherein the intersection between the first trajectory and the second trajectory is based on the first and second entrance positions, the first and second exit positions, and the reference indicia.

3. The method of claim 2, further comprising:
   developing the dosimeter film after the irradiating steps; and
   digitizing the developed film to provide at least three digital images of radiation beam patterns before the determining step;
   wherein the irradiating steps comprise irradiating the film so that the reference indicia provides a visible mark on developed and digitized images.

4. The method of claim 1, further comprising:
   locating an estimated isocenter of the radiation treatment device prior to irradiation;
   positioning an isocenter reference location defined by the phantom at the estimated isocenter; and
   electronically comparing the phantom isocenter reference location to the estimated isocenter location based on the determining step to evaluate the position and offset of the estimated isocenter location from center.

5. A method of evaluating an isocenter location of a radiation treatment device, the method comprising:
   obtaining a plurality of two dimensional digital images of radiation patterns taken from a plurality of different sides of a three-dimensional phantom;
   electronically generating a three-dimensional visual representation of a radiation isocenter using data from the two dimensional digital images;
   defining a reference coordinate system with respect to the three-dimensional phantom device using a reference location based on data obtained from a generally planar dosimeter sheet irradiated while supported by the phantom;

determining a spaced apart entrance location and an exit location for at least two different beam trajectories based on data obtained from the irradiated dosimeter sheet; and determining an intersection between the at least two beam trajectories with respect to the reference coordinate system of the phantom device based on the at least two beam trajectories to define an isocenter.

6. A method according to claim 5, wherein the radiation patterns correspond to an entrance radiation pattern providing a corresponding digitized image having a plurality of lines that intersect at at least one location.

7. The method of claim 5, further comprising:

defining an estimated isocenter with respect to the reference coordinate system in the phantom device; and electronically comparing the intersection to the estimated isocenter.

8. A computer program product for determining an isocenter location of a radiation treatment device, the computer program product comprising:

a computer readable medium having computer readable program code embodied therein, the computer readable program code comprising:

computer readable program code that is configured to convert a plurality of two dimensional digital images of radiation patterns taken from a plurality of different sides of a three-dimensional phantom into a three-dimensional visual representation of location and size of a radiation isocenter using data from the two dimensional digital images and data associated with a known geometric shape of the phantom;

computer readable program code that is configured to define a reference coordinate system with respect to the three-dimensional phantom device using a reference location based on data obtained from a digitized generally planar dosimeter sheet irradiated while supported by the phantom device;

computer readable program code that is configured to determine a spaced apart entrance location and an exit location for at least two different beam trajectories based on data obtained from the digital images; and computer readable program code that is configured to determine an intersection between the at least two beam trajectories with respect to the reference coordinate system of the phantom device based on the at least two beam trajectories.

9. A system of generating 3-D visualizations of a radiation isocenter of a radiation treatment system comprising:

a radiation treatment system;

a three-dimensional phantom having a known geometric shape and center; and a processor having computer readable medium having computer readable program code embodied therein, the computer readable program code comprising:

computer readable program code that is configured to convert a plurality of two dimensional digital images of radiation patterns taken from a plurality of different sides of the three-dimensional phantom into a three-dimensional visual representation of a radiation isocenter using data from the two dimensional digital images;

computer program code that calculates any deviation from center of the radiation isocenter of the radiation treatment system using data from the digital images of the radiation patterns, wherein the radiation patterns of the digital images comprise an entrance radiation pattern and at least two corresponding exit radiation patterns, with the entrance radiation pattern comprising a plurality of lines that have at least one intersecting position in the image.

10. A system of generating 3-D visualizations of a radiation isocenter of a radiation treatment system comprising:

a radiation treatment system;

a three-dimensional phantom having a known geometric shape and center; and a processor having computer readable medium having computer readable program code embodied therein, the computer readable program code comprising:

computer readable program code that is configured to convert a plurality of two dimensional digital images of radiation patterns taken from a plurality of different sides of the three-dimensional phantom into a three-dimensional visual representation of a radiation isocenter using data from the two dimensional digital images;

computer program code that calculates any deviation from center of the radiation isocenter of the radiation treatment system using data from the digital images of the radiation patterns, wherein at least one radiation sensitive dosimeter sheet configured to conform to at least one side of the phantom, the phantom having a substantially triangular cross-sectional shape, the at least one radiation sensitive dosimeter sheet having at least one reference indicia of a phantom side and/or front to back location relative to a position on the phantom.

* * * * *